(12) United States Patent
Kimmel et al.

(10) Patent No.: US 12,014,491 B2
(45) Date of Patent: Jun. 18, 2024

(54) CORRECTING MOTION-RELATED DISTORTIONS IN RADIOGRAPHIC SCANS

(71) Applicants: TECHNION RESEARCH & DEVELOPMENT FOUNDATION LIMITED, Haifa (IL); NEW YORK SOCIETY FOR THE RELIEF OF THE RUPTURED AND CRIPPLED, MAINTAINING THE HOSPITAL FOR SPECIAL SURGERY, New York, NY (US)

(72) Inventors: Ron Kimmel, Haifa (IL); Benjamin Groisser, Haifa (IL); Alon Wolf, Haifa (IL); Roger F. Widmann, New York, NY (US); Howard J. Hillstrom, New York, NY (US)

(73) Assignees: TECHNION RESEARCH & DEVELOPMENT FOUNDATION LIMITED, Haifa (IL); NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 569 days.

(21) Appl. No.: 17/271,651

(22) PCT Filed: Aug. 28, 2019

(86) PCT No.: PCT/IL2019/050968
§ 371 (c)(1),
(2) Date: Feb. 26, 2021

(87) PCT Pub. No.: WO2020/044345
PCT Pub. Date: Mar. 5, 2020

(65) Prior Publication Data
US 2021/0350532 A1 Nov. 11, 2021

Related U.S. Application Data

(60) Provisional application No. 62/723,610, filed on Aug. 28, 2018.

(51) Int. Cl.
G06T 7/00 (2017.01)
A61B 6/00 (2006.01)
(Continued)

(52) U.S. Cl.
CPC .......... *G06T 7/0012* (2013.01); *A61B 6/4411* (2013.01); *A61B 6/527* (2013.01);
(Continued)

(58) Field of Classification Search
CPC ......... G06T 7/0012; G06T 7/246; G06T 7/38; G06T 11/006; G06T 2207/10028;
(Continued)

(56) References Cited

U.S. PATENT DOCUMENTS

2004/0136490 A1 7/2004 Edic et al.
2005/0054910 A1* 3/2005 Tremblay ............... A61B 90/39
600/414
(Continued)

FOREIGN PATENT DOCUMENTS

EP 3146900 A1 * 3/2017 ............. A61B 6/00
EP 3146900 A1 3/2017
(Continued)

OTHER PUBLICATIONS

3D Reconstruction of Scoliotic Spines from Stereoradiography and Depth Imaging by Benjamin Groisser received on Dec. 25, 2017 and published on Apr. 23, 2018 (Year: 2018).*
(Continued)

Primary Examiner — Nizar N Sivji

(74) *Attorney, Agent, or Firm* — The Roy Gross Law Firm, LLC; Roy Gross

(57) ABSTRACT

A method comprising: receiving a radiographic image dataset representing a sequential radiographic scan of a region of a human subject; receiving three-dimensional (3D) image data representing an optical scan of a surface of said region, wherein said 3D image data is performed simultaneously with said sequential radiographic scan; estimating a time-dependent motion of said subject during said acquisition, relative to a specified position, based, at least in part, on said 3D image data; and using said estimating to determine corrections for said radiographic image dataset, based, at least in part, on a known transformation between corresponding coordinate systems of said radiographic image dataset and said 3D image data.

15 Claims, 17 Drawing Sheets

(51) Int. Cl.
  *G06T 7/246* (2017.01)
  *G06T 7/38* (2017.01)
  *G06T 11/00* (2006.01)
(52) U.S. Cl.
  CPC ............... *G06T 7/246* (2017.01); *G06T 7/38* (2017.01); *G06T 11/006* (2013.01); *G06T 2207/10028* (2013.01); *G06T 2207/10084* (2013.01); *G06T 2207/20201* (2013.01); *G06T 2207/30012* (2013.01); *G06T 2211/408* (2013.01)
(58) Field of Classification Search
  CPC . G06T 2207/10084; G06T 2207/20201; G06T 2207/30012; G06T 2211/408; G06T 2207/10016; G06T 2207/10116; G06T 5/003; G06T 5/50; A61B 6/4411; A61B 6/5247; A61B 6/527; A61B 6/032; A61B 6/488; A61B 6/5264; A61B 5/0077; A61B 5/1127; A61B 5/721; A61B 5/0035; A61B 2090/364; A61B 2090/3966; A61B 2576/00; G16H 30/40
  See application file for complete search history.

(56) References Cited

U.S. PATENT DOCUMENTS

| | | | | |
|---|---|---|---|---|
| 2005/0078799 | A1* | 4/2005 | Ancelin | G06T 5/003 378/154 |
| 2005/0238219 | A1 | 10/2005 | Roux et al. | |
| 2010/0121183 | A1* | 5/2010 | Taguchi | G06T 11/006 382/131 |
| 2021/0153943 | A1* | 5/2021 | Piron | A61B 34/25 |

FOREIGN PATENT DOCUMENTS

| | | | | |
|---|---|---|---|---|
| WO | WO-2005087107 | A1* | 9/2005 | A61B 6/481 |
| WO | WO-2015038607 | A2* | 3/2015 | A61B 18/02 |
| WO | WO-2017114685 | A1* | 7/2017 | A61B 6/481 |

OTHER PUBLICATIONS

Motion Compensated Fan-Beam Reconstruction for Nonrigid Transformation—Jul. 2008 (Year: 2008).*

Wood GA, Marshall RN. The accuracy of DLT extrapolation in three-dimensional film analysis. J Biomech. 1986;19(9):781-5. doi: 10.1016/0021-9290(86)90201-0. PMID: 3793752.

Rumelhart, D., Hinton, G. & Williams, R. Learning representations by back-propagating errors. Nature 323, 533-536 (1986). https://doi.org/10.1038/323533a0.

Carter OD, Haynes SG. Prevalence rates for scoliosis in US adults: results from the first National Health and Nutrition Examination Survey. Int J Epidemiol. Dec. 1987;16(4):537-44. doi: 10.1093/ije/16.4.537. PMID: 3501989.

Drerup B, Hierholzer E. Movement of the human pelvis and displacement of related anatomical landmarks on the body surface. J Biomech. 1987;20(10):971-7. doi: 10.1016/0021-9290(87)90326-5. PMID: 3693378.

Dansereau, J., & Stokes, I. A. F. (1988). Measurements of the three-dimensional shape of the rib cage. Journal of Biomechanics, 21(11), 893-901. doi:10.1016/0021-9290(88)90127-3.

E. Hierholzer and B. Drerup "Assessment of Three-Dimensional Scoliotic Deformity by Rasterstereography", Proc. SPIE 1030, Biostereometrics '88, (Apr. 14, 1989); https://doi.org/10.1117/12.950448.

Adams LP, Constant DA. Biostereometrics in the study of the morphology of the lumbar sacral spine. Med Biol Eng Comput. Jul. 1988;26(4):383-8. doi: 10.1007/BF02442296. PMID: 3255846.

Stokes IA, Shuma-Hartswick D, Moreland MS. Spine and back-shape changes in scoliosis. Acta Orthop Scand. Apr. 1988;59(2):128-33. PMID: 3364179. DOI: 10.1080/17453678809169692.

Gardner, M. (1988). Time travel and other mathematical bewilderments. New York: W.H. Freeman.

Turner-Smith AR, Harris JD, Houghton GR, Jefferson RJ. A method for analysis of back shape in scoliosis. J Biomech. 1988;21(6):497-509. doi: 10.1016/0021-9290(88)90242-4. PMID: 3209594.

B. Drerup and E. Hierholzer "Description of Scoliotic Deformity Pattern by Harmonic Functions", Proc. SPIE 1030, Biostereometrics '88, (Apr. 14, 1989); https://doi.org/10.1117/12.950447.

Groisser, B., Widmann, R., Hillstrom, H., Kimmel, R., & Wolf, A. (Jul. 2019). Motion Correction for Slot Scanners via Simultaneous Depth Imaging. 25th Congress of the European Society of Biomechanics, Vienna, Austria.

Suzuki S, Yamamuro T, Shikata J, Shimizu K, Iida H. Ultrasound measurement of vertebral rotation in idiopathic scoliosis. J Bone Joint Surg Br. Mar. 1989;71(2):252-5. doi: 10.1302/0301-620X.71B2.2647754. PMID: 2647754.

Carr AJ, Jefferson RJ, Turner-Smith AR, Weisz I, Thomas DC, Stavrakis T, Houghton GR. Surface stereophotogrammetry of thoracic kyphosis. Acta Orthop Scand. Apr. 1989;60(2):177-80. doi: 10.3109/17453678909149248. PMID: 2728878.

Denk W, Strickler JH, Webb WW. Two-photon laser scanning fluorescence microscopy. Science. Apr. 6, 1990;248(4951):73-6. doi: 10.1126/science.2321027. PMID: 2321027.

Seppälä, M., & Sorvali, T. (1991). Traces of commutators of Mobius transformations. Mathematica Scandinavica, 68, 53-58. https://doi.org/10.7146/math.scand.a-12345.

Drerup B, Hierholzer E. Evaluation of frontal radiographs of scoliotic spines—Part II. Relations between lateral deviation, lateral tilt and axial rotation of vertebrae. J Biomech. Dec. 1992;25(12):1443-50. doi: 10.1016/0021-9290(92)90057-8. PMID: 1337085.

Geman, S., McClure, D.E., & Geman, D. (1992). A nonlinear filter for film restoration and other problems in image processing. CVGIP Graph. Model. Image Process., 54, 281-289. DOI: 10.1016/1049-9652(92)90075-9.

Drerup B, Hierholzer E. Back shape measurement using video rasterstereography and three-dimensional reconstruction of spinal shape. Clin Biomech (Bristol, Avon). Jan. 1994;9(1):28-36. doi: 10.1016/0268-0033(94) 90055-8. PMID: 23916075.

Labelle H, Dansereau J, Bellefleur C, Jequier JC. Variability of geometric measurements from three-dimensional reconstructions of scoliotic spines and rib cages. Eur Spine J. 1995;4(2):88-94. doi: 10.1007/BF00278918. PMID: 7600156.

Drerup B, Hierholzer E. Assessment of scoliotic deformity from back shape asymmetry using an improved mathematical model. Clin Biomech (Bristol, Avon). Oct. 1996;11(7):376-383. doi: 10.1016/0268-0033(96)00025-3. PMID: 11415649.

(56) References Cited

OTHER PUBLICATIONS

Levy AR, Goldberg MS, Mayo NE, Hanley JA, Poitras B. Reducing the lifetime risk of cancer from spinal radiographs among people with adolescent idiopathic scoliosis. Spine (Phila Pa 1976). Jul. 1, 1996;21(13):1540-7; discussion 1548. doi: 10.1097/00007632-199607010-00011. PMID: 8817782.

Labelle H, Dansereau J, Bellefleur C, Poitras B. Three-dimensional effect of the Boston brace on the thoracic spine and rib cage. Spine (Phila Pa 1976). Jan. 1, 1996;21(1):59-64. doi: 10.1097/00007632-199601010-00013. Erratum in: Spine Apr. 1, 1996;21(7):890. PMID: 9122764.

Sobush DC, Simoneau GG, Dietz KE, Levene JA, Grossman RE, Smith WB. The lennie test for measuring scapular position in healthy young adult females: a reliability and validity study. J Orthop Sports Phys Ther. Jan. 1996;23(1):39-50. doi: 10.2519/jospt.1996.23.1.39. PMID: 8749749.

Scutt ND, Dangerfield PH, Dorgan JC. The relationship between surface and radiological deformity in adolescent idiopathic scoliosis: effect of change in body position. Eur Spine J. 1996;5(2):85-90. doi: 10.1007/BF00298386. PMID: 8724187.

Aubin CE, Dansereau J, Parent F, Labelle H, de Guise JA. Morphometric evaluations of personalised 3D reconstructions and geometric models of the human spine. Med Biol Eng Comput. Nov. 1997;35(6):611-8. doi: 10.1007/BF02510968. PMID: 9538536.

Weiss, Hans-Rudolf & Lohschmidt, K. & Obeidi, N.. (1997). Trunk deformity in relation to breathing. a comparative analysis with the formetric system. 37. 323-326. 10.3233/978-1-60750-881-6-323.

Theologis TN, Fairbank JC, Turner-Smith AR, Pantazopoulos T. Early detection of progression in adolescent idiopathic scoliosis by measurement of changes in back shape with the Integrated Shape Imaging System scanner. Spine (Phila Pa 1976). Jun. 1, 1997;22(11):1223-7; discussion 1228. doi: 10.1097/00007632-199706010-00010. PMID: 9201860.

Aubin CE, Dansereau J, Petit Y, Parent F, de Guise JA, Labelle H. Three-dimensional measurement of wedged scoliotic vertebrae and intervertebral disks. Eur Spine J. 1998;7(1):59-65. doi: 10.1007/s005860050029. PMID: 9548361; PMCID: PMC3615358.

Kalifa G, Charpak Y, Maccia C, Fery-Lemonnier E, Bloch J, Boussard JM, Attal M, Dubousset J, Adamsbaum C. Evaluation of a new low-dose digital x-ray device: first dosimetric and clinical results in children. Pediatr Radiol. Jul. 1998;28(7):557-61. doi: 10.1007/s002470050413. PMID: 9662585.

Jianhua Yao, Joseph E. Burns, Hector Muñoz and Ronald M. Summers, Detection of Vertebral Body Fractures Based on Cortical Shell Unwrapping, International Conference on Medical Image Computing and Computer Assisted Intervention, vol. 7512, 2012, pp. 509-516.

Karachalios T, Sofianos J, Roidis N, Sapkas G, Korres D, Nikolopoulos K. Ten-year follow-up evaluation of a school screening program for scoliosis. Is the forward-bending test an accurate diagnostic criterion for the screening of scoliosis? Spine (Phila Pa 1976). Nov. 15, 1999;24(22):2318-24. doi: 10.1097/00007632-199911150-00006. PMID: 10586455.

Cheriet, Farida & Dansereau, Jean & Petit, Yvan & Aubin, Carl-Eric & Labelle, Hubert & de Guise, Jacques. (1999). Towards the Self-Calibration of a Multiview Radiographic Imaging System for the 3D Reconstruction of the Human Spine and Rib Cage . . . IJPRAI. 13. 761-779. 10.1142/S0218001499000434.

Lathauwer, Lieven & De Moor, Bart. (2000). A Multi-Linear Singular Value Decomposition. Society for Industrial and Applied Mathematics. 21. 1253-1278. 10.1137/S0895479896305696.

Oxborrow NJ. Assessing the child with scoliosis: the role of surface topography. Arch Dis Child. Nov. 2000;83(5):453-5. doi: 10.1136/adc.83.5.453. PMID: 11040160; PMCID: PMC1718548.

Laporte, S., Mitton, D., Ismael, B. et al. Quantitative morphometric study of thoracic spine A preliminary parameters statistical analysis. Eur J Orthop Surg Traumatol 10, 85-91 (2000). https://doi.org/10.1007/BF02803102.

Mitton D, Landry C, Veron S, Skalli W, Lavaste F, De Guise JA. 3D reconstruction method from biplanar radiography using non-stereocorresponding points and elastic deformable meshes. Med Biol Eng Comput. Mar. 2000;38(2):133-9. doi: 10.1007/BF02344767. PMID: 10829404.

Doody MM, Lonstein JE, Stovall M, Hacker DG, Luckyanov N, Land CE. Breast cancer mortality after diagnostic radiography: findings from the U.S. Scoliosis Cohort Study. Spine (Phila Pa 1976). Aug. 15, 2000;25(16):2052-63. doi: 10.1097/00007632-200008150-00009. PMID: 10954636.

Poncet P, Delorme S, Ronsky JL, Dansereau J, Clynch G, Harder J, Dewar RD, Labelle H, Gu PH, Zemnicke RF. Reconstruction of laser-scanned 3D torso topography and stereoradiographical spine and rib-cage geometry in scoliosis. Comput Methods Biomech Biomed Engin. 2000;4(1):59-75. doi: 10.1080/10255840008907998. PMID: 1264861.

Lenke LG, Betz RR, Harms J, Bridwell KH, Clements DH, Lowe TG, Blanke K. Adolescent idiopathic scoliosis: a new classification to determine extent of spinal arthrodesis. J Bone Joint Surg Am. Aug. 2001;83(8):1169-81. PMID: 11507125.

Loram, I. D., Kelly, S. M., & Lakie, M. (2001). Human balancing of an inverted pendulum: is sway size controlled by ankle impedance?. The Journal of physiology, 532(Pt 3), 879-891. https://doi.org/10.1111/j.1469-7793.2001.0879e.x.

Goldberg CJ, Kaliszer M, Moore DP, Fogarty EE, Dowling FE. Surface topography, Cobb angles, and cosmetic change in scoliosis. Spine (Phila Pa 1976). Feb. 15, 2001;26(4):E55-63. doi: 10.1097/00007632-200102150-00005. PMID: 11224901.

Mitulescu A, Semaan I, De Guise JA, Leborgne P, Adamsbaum C, Skalli W. Validation of the non-stereo corresponding points stereoradiographic 3D reconstruction technique. Med Biol Eng Comput. Mar. 2001;39(2):152-8. doi: 10.1007/BF02344797. PMID: 11361240.

Boice JD Jr. Radiation and breast carcinogenesis. Med Pediatr Oncol. May 2001;36(5):508-13. doi: 10.1002/mpo.1122. PMID: 11340604.

Jaremko JL, Poncet P, Ronsky J, Harder J, Dansereau J, Labelle H, Zernicke RF. Estimation of spinal deformity in scoliosis from torso surface cross sections. Spine (Phila Pa 1976). Jul. 15, 2001;26(14):1583-91. doi: 10.1097/00007632-200107150-00017. PMID: 11462091.

Jaremko JL, Poncet P, Ronsky J, Harder J, Dansereau J, Labelle H, Zernicke RF. Indices of torso asymmetry related to spinal deformity in scoliosis. Clin Biomech (Bristol, Avon). Oct. 2002;17(8):559-68. doi: 10.1016/s0268-0033(02)00099-2. PMID: 12243715.

Parent S, Labelle H, Mitulescu A, Latimer B, Skalli W, Lavaste F, de Guise J. Morphometric analysis of one anatomic scoliotic specimen. Stud Health Technol Inform. 2002;88:387-92. PMID: 15456067.

Mitulescu A, Skalli W, Mitton D, De Guise JA. Three-dimensional surface rendering reconstruction of scoliotic vertebrae using a non stereo-corresponding points technique. Eur Spine J. Aug. 2002;11(4):344-52. doi: 10.1007/s00586-002-0432-8. Epub Jun. 26, 2002. PMID: 12193996; PMCID: PMC3610474.

Gurney B. Leg length discrepancy. Gait Posture. Apr. 2002;15(2):195-206. doi: 10.1016/s0966-6362(01)00148-5. PMID: 11869914.

Kuklo TR, Lenke LG, Graham EJ, Won DS, Sweet FA, Blanke KM, Bridwell KH. Correlation of radiographic, clinical, and patient assessment of shoulder balance following fusion versus nonfusion of the proximal thoracic curve in adolescent idiopathic scoliosis. Spine (Phila Pa 1976). Sep. 15, 2002;27(18):2013-20. doi: 10.1097/00007632-200209150-00009. PMID: 12634561.

Ito, K., Hosoda, K., Shimizu, M. et al. Direct assessment of 3D foot bone kinematics using biplanar X-ray fluoroscopy and an automatic model registration method. J Foot Ankle Res 8, 21 (2015). https://doi.org/10.1186/s13047-015-0079-4.

Shane J. Latham, Andrew M. Kingston, Benoit Recur, Glenn R. Myers, Adrian P. Sheppard, "Multi-resolution radiograph alignment for motion correction in x-ray micro-tomography," Proc. SPIE 9967, Developments in X-Ray Tomography X, 996710 (Oct. 3, 2016); https://doi.org/10.1117/12.2238259.

Qin L, van Gelderen P, Derbyshire JA, Jin F, Lee J, de Zwart JA, Tao Y, Duyn JH. Prospective head-movement correction for high-resolution MRI using an in-bore optical tracking system. Magn Reson Med. Oct. 2009;62(4):924-34. doi: 10.1002/mrm.22076. PMID: 19526503; PMCID: PMC3523280.

(56) References Cited

OTHER PUBLICATIONS

Liying Zheng, Kang Li, Snehal Shetye, Xudong Zhang, Integrating dynamic stereo-radiography and surface-based motion data for subject-specific musculoskeletal dynamic modeling, Journal of Biomechanics, vol. 47, Issue 12, 2014, pp. 3217-3221, ISSN 0021-9290, https://doi.org/10.1016/j.jbiomech.2014.08.009.

André, B., Dansereau, J., & Labelle, H. (1994). Optimized vertical stereo base radiographic setup for the clinical three-dimensional reconstruction of the human spine. Journal of Biomechanics, 27(8), 1023-1035. doi:10.1016/0021-9290(94)90219-4.

Dragomir Anguelov, Praveen Srinivasan, Daphne Koller, Sebastian Thrun, Jim Rodgers, and James Davis. 2005. SCAPE: shape completion and animation of people. ACM Trans. Graph. 24, 3 (Jul. 2005), 408-416. DOI:https://doi.org/10.1145/1073204.1073207.

Arun KS, Huang TS, Blostein SD. Least-squares fitting of two 3-d point sets. IEEE Trans Pattern Anal Mach Intell. May 1987;9(5):698-700. doi: 10.1109/tpami.1987.4767965. PMID: 21869429.

Blumer SL, Dinan D, Grissom LE. Benefits and unexpected artifacts of biplanar digital slot-scanning imaging in children. Pediatr Radiol. Jul. 2014;44(7):871-82. doi: 10.1007/s00247-014-2908-1. Epub Feb. 22, 2014. Erratum in: Pediatr Radiol. Jul. 2014;44(7):904. PMID: 24563147.

Charpak, G & Derré, J & Giomataris, Y & Rebourgeard, Ph. (2002). Micromegas, a multipurpose gaseous detector. Nuclear Instruments and Methods in Physics Research Section A: Accelerators, Spectrometers, Detectors and Associated Equipment. 478. 26-36. 10.1016/S0168-9002(01)01713-2.

F. Cheriet, C. Laporte, S. Kadoury, H. Labelle and J. Dansereau, "A Novel System for the 3-D Reconstruction of the Human Spine and Rib Cage From Biplanar X-Ray Images," in IEEE Transactions on Biomedical Engineering, vol. 54, No. 7, pp. 1356-1358, Jul. 2007, doi: 10.1109/TBME.2006.889205.

Choi JH, Maier A, Keil A, Pal S, McWalter EJ, Beaupre GS, Gold GE, Fahrig R. Fiducial marker-based correction for involuntary motion in weight-bearing C-arm CT scanning of knees. II. Experiment. Med Phys. Jun. 2014;41(6):061902. doi: 10.1118/1.4873675. PMID: 24877813; PMCID: PMC4008764.

De Korvin G, Randriaminahisoa T, Cugy E, Cheze L, de Sèze M. Detection of progressive idiopathic scoliosis during growth using back surface topography: a prospective study of 100 patients. Ann Phys Rehabil Med. Dec. 2014;57(9-10):629-39. doi: 10.1016/j.rehab.2014.09.002. Epub Sep. 19, 2014. PMID: 25267453.

Drerup B, Hierholzer E. Automatic localization of anatomical landmarks on the back surface and construction of a body-fixed coordinate system. J Biomech. 1987;20(10):961-70. doi: 10.1016/0021-9290(87)90325-3. PMID: 3693377.

Diana A Glaser and Lawrence Lenke. 3D Upright Slot-Scanner EOS vs Supine CT: A Clinical Examination. ORS 2014 Annual Meeting. In ORS, pp. 2-4, 2012.

Groisser B, Kimmel R, Feldman G, Rozen N, Wolf A. 3D Reconstruction of Scoliotic Spines from Stereoradiography and Depth Imaging. Ann Biomed Eng. Aug. 2018;46(8):1206-1215. doi: 10.1007/s10439-018-2033-7. Epub Apr. 23, 2018. PMID: 29687237.

Illés T, Somoskeoy S. The EOS™ imaging system and its uses in daily orthopaedic practice. Int Orthop. Jul. 2012;36(7):1325-31. doi: 10.1007/s00264-012-1512-y. Epub Feb. 28, 2012. PMID: 22371113; PMCID: PMC3385897.

Legaye J, Saunier P, Dumas R, Vallee C. Correction for patient sway in radiographic biplanar imaging for three-dimensional reconstruction of the spine: in vitro study of a new method. Acta Radiol. Sep. 2009;50(7):781-90. doi: 10.1080/02841850903036272. PMID: 19551533.

Matthew Loper, Naureen Mahmood, Javier Romero, Gerard Pons-Moll, and Michael J. Black. 2015. SMPL: a skinned multi-person linear model. ACM Trans. Graph. 34, 6, Article 248 (Nov. 2015), 16 pages. DOI:https://doi.org/10.1145/2816795.2818013.

Marchant TE, Price GJ, Matuszewski BJ, Moore CJ. Reduction of motion artefacts in on-board cone beam CT by warping of projection images. Br J Radiol. Mar. 2011;84(999):251-64. doi: 10.1259/bjr/90983944. Epub Nov. 16, 2010. PMID: 21081580; PMCID: PMC3473871.

Maurer C, Peterka RJ. A new interpretation of spontaneous sway measures based on a simple model of human postural control. J Neurophysiol. Jan. 2005;93(1):189-200. doi: 10.1152/jn.00221.2004. Epub Aug. 25, 2004. Erratum in: J Neurophysiol. Jun. 2005;93(6):3720. PMID: 15331614.

Melhem E, Assi A, El Rachkidi R, Ghanem I. EOS(®) biplanar X-ray imaging: concept, developments, benefits, and limitations. J Child Orthop. Feb. 2016;10(1):1-14. doi: 10.1007/s11832-016-0713-0. Epub Feb. 16, 2016. PMID: 26883033; PMCID: PMC4763151.

Daniel C. Moura, Jorge G. Barbosa, Ana M. Reis, and Joao Manuel R S Tavares. A flexible approach for the calibration of biplanar radiography of the spine on conventional radiological systems. CMES—Computer Modeling in Engineering and Sciences, 60(2):115-137, 2010. doi:10.3970/cmes.2010.060.115.

Mukherjee JM, McNamara JE, Johnson KL, Dey J, King MA. Estimation of Rigid-Body and Respiratory Motion of the Heart From Marker-Tracking Data for SPECT Motion Correction. IEEE Trans Nucl Sci. Feb. 2009;56(1):147-155. doi: 10.1109/TNS.2008.2010319. PMID: 20539825; PMCID: PMC2882690.

Olesen, Oline & Wilm, Jakob & Paulsen, Roger & Højgaard, Liselotte & Larsen, Rasmus. (2014). DLP Technology Application: 3D Head Tracking and Motion Correction in Medical Brain Imaging. Proceedings of SPIE—The International Society for Optical Engineering. 8979. 10.1117/12.2035374.

Pearcy MJ. Stereo radiography of lumbar spine motion. Acta Orthop Scand Suppl. 1985;212:1-45. doi: 10.3109/17453678509154154. PMID: 3859987.

M. Prummer, J. Hornegger, G. Lauritsch, L. Wigstrom, E. Girard-Hughes and R. Fahrig, "Cardiac C-Arm CT: A Unified Framework for Motion Estimation and Dynamic CT," in IEEE Transactions on Medical Imaging, vol. 28, No. 11, pp. 1836-1849, Nov. 2009, doi: 10.1109/TMI.2009.2025499.

Tzou CH, Artner NM, Pona I, Hold A, Placheta E, Kropatsch WG, Frey M. Comparison of three-dimensional surface-imaging systems. J Plast Reconstr Aesthet Surg. Apr. 2014;67(4):489-97. doi: 10.1016/j.bjps.2014.01.003. Epub Jan. 15, 2014. PMID: 24529695.

Luo TD, Stans AA, Schueler BA, Larson AN. Cumulative Radiation Exposure With EOS Imaging Compared With Standard Spine Radiographs. Spine Deform. Mar. 2015;3(2):144-150. doi: 10.1016/j.jspd.2014.09.049. Epub Mar. 4, 2015. PMID: 27927305.

Day, B. L., Steiger, M. J., Thompson, P. D., & Marsden, C. D. (1993). Effect of vision and stance width on human body motion when standing: implications for afferent control of lateral sway. The Journal of physiology, 469, 479-499. https://doi.org/10.1113/jphysiol.1993.sp019824.

Nault ML, Allard P, Hinse S, Le Blanc R, Caron O, Labelle H, Sadeghi H. Relations between standing stability and body posture parameters in adolescent idiopathic scoliosis. Spine (Phila Pa 1976). Sep. 1, 2002;27(17):1911-7. doi: 10.1097/00007632-200209010-00018. PMID: 12221357.

Simon, A.L., Ferrero, E., Larson, A.N et al. Stereoradiography imaging motion artifact: does it affect radiographic measures after spinal instrumentation?. Eur Spine J 27, 1105-1111 (2018) orig pub 2016. https://doi.org/10.1007/s00586-016-4462-z.

M. Tremblay, F. Tam, and S. J. Graham, "Retrospective coregistration of functional magnetic resonance imaging data using external monitoring," Magnetic Resonance in Medicine, vol. 53, No. 1, pp. 141-149, 2005. https://doi.org/10.1002/mrm.20319.

Dold C, Zaitsev M, Speck O, Firle EA, Hennig J, Sakas G. Advantages and limitations of prospective head motion compensation for MRI using an optical motion tracking device. Acad Radiol. Sep. 2006;13(9):1093-103. doi: 10.1016/j.acra.2006.05.010. PMID: 16935721.

Stokes IA. Three-dimensional terminology of spinal deformity. A report presented to the Scoliosis Research Society by the Scoliosis Research Society Working Group on 3-D terminology of spinal deformity. Spine (Phila Pa 1976). Jan. 15, 1994;19(2):236-48. PMID: 8153835.

Groisser, B. (2019). Geometry of the EOS (R) Radiographic Scanner. arXiv preprint arXiv:1904.06711.

(56) References Cited

OTHER PUBLICATIONS

Boisvert J, Cheriet F, Pennec X, Labelle H, Ayache N. Geometric variability of the scoliotic spine using statistics on articulated shape models. IEEE Trans Med Imaging. Apr. 2008;27(4):557-68. doi: 10.1109/TMI.2007.911474. PMID: 18390352.
J. Boisvert, X. Pennec, N. Ayache, H. Labelle and K. Cheriet, "3D anatomical variability assessment of the scoliotic spine using statistics on Lie groups," 3rd IEEE International Symposium on Biomedical Imaging: Nano to Macro, 2006., 2006, pp. 750-753, doi: 10.1109/ISBI.2006.1625025.
Yao, J., Burns, J. E., Forsberg, D., Seitel, A., Rasoulian, A., Abolmaesumi, P., Hammernik, K., Urschler, M., Ibragimov, B., Korez, R., Vrtovec, T., Castro-Mateos, I., Pozo, J. M., Frangi, A. F., Summers, R. M., & Li, S. (2016). A multi-center milestone study of clinical vertebral CT segmentation. Computerized medical imaging and graphics : the official journal of the Computerized Medical Imaging Society, 49, 16-28. https://doi.org/10.1016/j.compmedimag.2015.12.006.
Tesic MM, Piccaro MF, Munier B. Full field digital mammography scanner. Eur J Radiol. Jul. 1999;31(1):2-17. doi: 10.1016/s0720-048x(99)00064-9. PMID: 10477093.
Drerup B. Improvements in measuring vertebral rotation from the projections of the pedicles. J Biomech. 1985;18(5):369-78. doi: 10.1016/0021-9290(85)90292-1. PMID: 4008507.
Panjabi MM, Brand RA Jr, White AA 3rd. Three-dimensional flexibility and stiffness properties of the human thoracic spine. J Biomech. 1976;9(4):185-92. doi: 10.1016/0021-9290(76)90003-8. PMID: 1262353.
Gerchberg, R.W. (1972). A practical algorithm for the determination of phase from image and diffraction plane pictures. Optik, 35, 237-246.
Branko Grünbaum, G. C. Shephard. "Tilings with congruent tiles." Bulletin (New Series) of the American Mathematical Society, 3(3) 951-973 Nov. 1980. https://doi.org/bams/1183547682.
Robin GC, Span Y, Steinberg R, Makin M, Menczel J. Scoliosis in the elderly: a follow-up study. Spine (Phila Pa 1976). Jul.-Aug. 1982;7(4):355-9. doi: 10.1097/00007632-198207000-00005. PMID: 6215719.
Frobin W, Hierholzer E. Analysis of human back shape using surface curvatures. J Biomech. 1982;15(5):379-90. doi: 10.1016/0021-9290(82)90059-8. PMID: 7118952.
Hierholzer E, Luxmann G. Three-dimensional shape analysis of the scoliotic spine using invariant shape parameters. J Biomech. 1982;15(8):583-98. doi: 10.1016/0021-9290(82)90070-7. PMID: 7142225.
Drerup, B. (1984). Principles of measurement of vertebral rotation from frontal projections of the pedicles. Journal of Biomechanics, 17(12), 923-935. doi:10.1016/0021-9290(84)90005-8.
Drerup B, Hierholzer E. Objective determination of anatomical landmarks on the body surface: measurement of the vertebra prominens from surface curvature. J Biomech. 1985;18(6):467-74. doi: 10.1016/0021-9290(85)90282-9. PMID: 4030803.
E. Hierholzer "Analysis of Left-Right Asymmetry of the Back Shape of Scoliotic Patients", Proc. SPIE 0602, Biostereometrics '85, (Jul. 7, 1986); https://doi.org/10.1117/12.956324.
Groisser, B. (Mar. 2022). Intermodal Human Body Modeling: Combining Radiography with Topographic Imaging for Non-ionizing Assessment of Adolescent Idiopathic Scoliosis. Technion—Israel Institute of Technology.
Jaremko JL, Poncet P, Ronsky J, Harder J, Dansereau J, Labelle H, Zernicke RF. Genetic algorithm-neural network estimation of cobb angle from torso asymmetry in scoliosis. J Biomech Eng. Oct. 2002;124(5):496-503. doi: 10.1115/1.1503375. PMID: 12405591.
Zubairi, Junaid. (2002). Applications of computer-aided raster stereography in spinal deformity detection. Image Vision Comput. . . 20. 319-324. 10.1016/S0262-8856(02)00026-4.
Sanders JO, Polly DW Jr, Cats-Baril W, Jones J, Lenke LG, O'Brien MF, Stephens Richards B, Sucato DJ; AIS Section of the Spinal Deformity Study Group. Analysis of patient and parent assessment of deformity in idiopathic scoliosis using the Walter Reed Visual Assessment Scale. Spine (Phila Pa 1976). Sep. 15, 2003;28(18):2158-63. doi: 10.1097/01.BRS.0000084629.97042.0B. PMID: 14501929.
Sacconi L, Froner E, Antolini R, Taghizadeh MR, Choudhury A, Pavone FS. Multiphoton multifocal microscopy exploiting a diffractive optical element. Opt Lett. Oct. 15, 2003;28(20):1918-20. doi: 10.1364/ol.28.001918. PMID: 14587775.
Allen, Brett & Curless, Brian & Popovic, Zoran. (2003). The Space of Human Body Shapes: Reconstruction and Parameterization from Range Scans. ACM Trans. Graph. . . 22. 587-594. 10.1145/1201775.882311.
Dumas R, Steib JP, Mitton D, Lavaste F, Skalli W. Three-dimensional quantitative segmental analysis of scoliosis corrected by the in situ contouring technique. Spine (Phila Pa 1976). Jun. 1, 2003;28(11):1158-62. doi: 10.1097/01.BRS.0000068242.29809.DO. PMID: 12782985.
Grier DG. A revolution in optical manipulation. Nature. Aug. 14, 2003;424(6950):810-6. doi: 10.1038/nature01935. PMID: 12917694.
Benameur S, Mignotte M, Parent S, Labelle H, Skalli W, de Guise J. 3D/2D registration and segmentation of scoliotic vertebrae using statistical models. Comput Med Imaging Graph. Sep.-Oct. 2003;27(5):321-37. doi: 10.1016/s0895-6111(03)00019-3. PMID: 12821026.
LeBras, Anthony & Laporte, Sebastien & Mitton, David & de Guise, Jacques & Skalli, Wafa. (2003). Three-dimensional (3D) detailed reconsruction of human vertebrae from low-dose digital stereoradiography. European Journal of Orthopaedic Surgery & Traumatology. 13. 57-62. 10.1007/s00590-003-0074-5.
Nagel G, Szellas T, Huhn W, Kateriya S, Adeishvili N, Berthold P, Ollig D, Hegemann P, Bamberg E. Channelrhodopsin-2, a directly light-gated cation-selective membrane channel. Proc Natl Acad Sci U S A. Nov. 25, 2003;100(24):13940-5. doi: 10.1073/pnas.1936192100. Epub Nov. 13, 2003. PMID: 14615590; PMCID: PMC283525.
Dumas R, Mitton D, Laporte S, Dubousset J, Steib JP, Lavaste F, Skalli W. Explicit calibration method and specific device designed for stereoradiography. J Biomech. Jun. 2003;36(6):827-34. doi: 10.1016/s0021-9290(03)00016-2. PMID: 12742450.
Delorme S, Petit Y, de Guise JA, Labelle H, Aubin CE, Dansereau J. Assessment of the 3-d reconstruction and high-resolution geometrical modeling of the human skeletal trunk from 2-D radiographic images. IEEE Trans Biomed Eng. Aug. 2003;50(8):989-98. doi: 10.1109/TBME.2003.814525. PMID: 12892326.
Dragomir Anguelov, Daphne Koller, Hoi-Cheung Pang, Praveen Srinivasan, and Sebastian Thrun. 2004. Recovering articulated object models from 3D range data. In Proceedings of the 20th conference on Uncertainty in artificial intelligence (UAI '04). AUAI Press, Arlington, Virginia, USA, 18-26.
Brèque, Cyril & Dupre, Jean-Christophe & Bremand, Fabrice. (2004). Calibration of a system of projection moiré for relief measuring: Biomechanical applications. Optics and Lasers in Engineering. 41. 241-260. 10.1016/S0143-8166(02)00198-7.
Robert W. Sumner and Jovan Popović. 2004. Deformation transfer for triangle meshes. ACM Trans. Graph. 23, 3 (Aug. 2004), 399-405. DOI:https://doi.org/10.1145/1015706.1015736.
Dumas R, Le Bras A, Champain N, Savidan M, Mitton D, Kalifa G, Steib JP, de Guise JA, Skalli W. Validation of the relative 3D orientation of vertebrae reconstructed by bi-planar radiography. Med Eng Phys. Jun. 2004;26(5):415-22. doi: 10.1016/j.medengphy.2004.02.004. PMID: 15147749.
Huysmans T, Haex B, Van Audekercke R, Vander Sloten J, Van der Perre G. Three-dimensional mathematical reconstruction of the spinal shape, based on active contours. J Biomech. Nov. 2004;37(11):1793-8. doi: 10.1016/j.jbiomech.2004.01.020. PMID: 15388323.
Pomero V, Mitton D, Laporte S, de Guise JA, Skalli W. Fast accurate stereoradiographic 3D-reconstruction of the spine using a combined geometric and statistic model. Clin Biomech (Bristol, Avon). Mar. 2004;19(3):240-7. doi: 10.1016/j.clinbiomech.2003.11.014. PMID: 15003338.
Sinclair G, Leach J, Jordan P, Gibson G, Yao E, Laczik Z, Padgett M, Courtial J. Interactive application in holographic optical tweezers of a multi-plane Gerchberg-Saxton algorithm for three-

(56) References Cited

OTHER PUBLICATIONS dimensional light shaping. Opt Express. Apr. 19, 2004;12(8):1665-70. doi: 10.1364/opex.12.001665. PMID: 19474992.

Zhu G, van Howe J, Durst M, Zipfel W, Xu C. Simultaneous spatial and temporal focusing of femtosecond pulses. Opt Express. Mar. 21, 2005;13(6):2153-9. doi: 10.1364/opex.13.002153. PMID: 19495103.

Hayasaki, Yoshio & Sugimoto, Takashi & Takita, Akihiro & Nishida, Nobuo. (2005). Variable holographic femtosecond laser processing by use of a spatial light modulator. Applied Physics Letters. 87. 031101-031101. 10.1063/1.1992668.

Bergeron, Charles & Cheriet, Farida & Ronsky, Janet & Zernicke, Ronald & Labelle, Hubert. (2005). Prediction of anterior scoliotic spinal curve from trunk surface using support vector regression. Engineering Applications of Artificial Intelligence. 18. 973-983. 10.1016/j.engappai.2005.03.006.

Benameur S, Mignotte M, Labelle H, De Guise JA. A hierarchical statistical modeling approach for the unsupervised 3-D biplanar reconstruction of the scoliotic spine. IEEE Trans Biomed Eng. Dec. 2005;52(12):2041-57. doi: 10.1109/TBME.2005.857665. PMID: 16366228.

Oron D, Tal E, Silberberg Y. Scanningless depth-resolved microscopy. Opt Express. Mar. 7, 2005;13(5):1468-76. doi: 10.1364/opex.13.001468. PMID: 19495022.

Bronstein, A.M., Bronstein, M.M. & Kimmel, R. Three-Dimensional Face Recognition. Int J Comput Vision 64, 5-30 (2005). https://doi.org/10.1007/s11263-005-1085-y.

Anguelov, Dragomir. 2005. Learning models of shape from 3D range data.

Huysmans T, Moens P, Van Audekercke R. An active shape model for the reconstruction of scoliotic deformities from back shape data. Clin Biomech (Bristol, Avon). Oct. 2005;20(8):813-21. doi: 10.1016/j.clinbiomech.2004.06.015. PMID: 15963614.

Knott P, Mardjetko S, Nance D, Dunn M. Electromagnetic topographical technique of curve evaluation for adolescent idiopathic scoliosis. Spine (Phila Pa 1976). Nov. 15, 2006;31(24):E911-5; discussion E916. doi: 10.1097/01.ors.0000245924.82359.ab. PMID: 17108820.

Hackenberg L, Hierholzer E, Bullmann V, Liljenqvist U, Götze C. Rasterstereographic analysis of axial back surface rotation in standing versus forward bending posture in idiopathic scoliosis. Eur Spine J. Jul. 2006;15(7):1144-9. doi: 10.1007/s00586-005-0057-9. Epub Jan. 21, 2006. PMID: 16429283; PMCID: PMC3233931.

Chi WM, Cheng CW, Yeh WC, Chuang SC, Chang TS, Chen JH. Vertebral axial rotation measurement method. Comput Methods Programs Biomed. Jan. 2006;81(1):8-17. doi: 10.1016/j.cmpb.2005.10.004. Epub Nov. 21, 2005. PMID: 16303206.

Keynan O, Fisher CG, Vaccaro A, Fehlings MG, Oner FC, Dietz J, Kwon B, Rampersaud R, Bono C, France J, Dvorak M. Radiographic measurement parameters in thoracolumbar fractures: a systematic review and consensus statement of the spine trauma study group. Spine (Phila Pa 1976). Mar. 1, 2006;31(5):E156-65. doi: 10.1097/01.brs.0000201261.94907.0d. PMID: 16508540.

Roweis, S. T., & Saul, L. K. (2000). Nonlinear dimensionality reduction by locally linear embedding. science, 290(5500), 2323-2326. doi:10.1126/science.290.5500.2323.

Rousseau MA, Laporte S, Chavary-Bernier E, Lazennec JY, Skalli W. Reproducibility of measuring the shape and three-dimensional position of cervical vertebrae in upright position using the EOS stereoradiography system. Spine (Phila Pa 1976). Nov. 1, 2007;32(23):2569-72. doi: 10.1097/BRS.0b013e318158cba2. PMID: 17978655.

Kadoury S, Cheriet F, Laporte C, Labelle H. A versatile 3D reconstruction system of the spine and pelvis for clinical assessment of spinal deformities. Med Biol Eng Comput. Jun. 2007;45(6):591-602. doi: 10.1007/s11517-007-0182-1. Epub May 26, 2007. PMID: 17530454.

Pazos V, Cheriet F, Danserau J, Ronsky J, Zernicke RF, Labelle H. Reliability of trunk shape measurements based on 3-D surface reconstructions. Eur Spine J. 2007;16(11):1882-1891. doi:10.1007/s00586-007-0457-0.

Scherl, S. A., Phillips, W., & Torchia, M. M. (2012). Adolescent idiopathic scoliosis: Clinical features, evaluation, and diagnosis. UpToDate®. UpToDate®: UpToDate.

Grivas TB, Vasiliadis ES, Mihas C, Savvidou O. The effect of growth on the correlation between the spinal and rib cage deformity: implications on idiopathic scoliosis pathogenesis. Scoliosis. Sep. 14, 2007;2:11. doi: 10.1186/1748-7161-2-11. PMID: 17868459; PMCID: PMC2040132.

Gille O, Champain N, Benchikh-El-Fegoun A, Vital JM, Skalli W. Reliability of 3D reconstruction of the spine of mild scoliotic patients. Spine (Phila Pa 1976). Mar. 1, 2007;32(5):568-73. doi: 10.1097/01.brs.0000256866.25747.b3. PMID: 17334292.

Janicki JA, Alman B. Scoliosis: Review of diagnosis and treatment. Paediatr Child Health. Nov. 2007;12(9):771-6. doi: 10.1093/pch/12.9.771. PMID: 19030463; PMCID: PMC2532872.

Martin RM, Fish DE. Scapular winging: anatomical review, diagnosis, and treatments. Curr Rev Musculoskelet Med. Mar. 2008;1(1):1-11. doi: 10.1007/s12178-007-9000-5. PMID: 19468892; PMCID: PMC2684151.

Mitton, D., Zhao, K., Bertrand, S., Zhao, C., Laporte, S., Yang, C., . . . Skalli, W. (2008). 3D reconstruction of the ribs from lateral and frontal X-rays in comparison to 3D CT-scan reconstruction. Journal of Biomechanics, 41(3), 706-710. doi:10.1016/j.jbiomech.2007.09.034.

Yao, J. (Dec. 6, 2018). SpineWeb : Main / Datasets : browse. SpineWeb. Retrieved Jul. 20, 2022, from http://spineweb.digitalimaginggroup.ca/Index.php?n=Main. Datasets.

3dMD Products. (Aug. 21, 2020). 3dMD, LLC. https://3dmd.com/products/#https://3dmd.com/products/#!/body.

* cited by examiner

CORRECTING MOTION-RELATED DISTORTIONS IN RADIOGRAPHIC SCANS

CROSS REFERENCE TO RELATED APPLICATIONS

This application is a National Phase of PCT Patent Application No. PCT/IL2019/050968 having International filing date of Aug. 28, 2019, which claims the benefit of priority from U.S. Provisional Patent Application No. 62/723,610, filed on Aug. 28, 2018, entitled "MOTION CORRECTION FOR SLOT SCANNERS USING SURFACE MEASUREMENTS", the contents of which are incorporated by reference herein in their entirety.

FIELD OF INVENTION

The present invention is in the field of computer imaging.

BACKGROUND OF THE INVENTION

Slot scanners have become a popular imaging technology for diagnosis and assessment of scoliosis, as the such systems can produce high contrast orthogonal radiographs with relatively low radiation exposure. However, slot scanning techniques have limitations not faced by traditional X-ray systems, most notably the fact that patient movement during the scan can distort the image.

Stereo radiography fills an important niche between planar radiography and computed tomography, allowing analysis of skeletal structure in load bearing posture. Although stereo images do not provide true three dimensional measurements, stereo-reconstruction allows for 3D analysis of targeted structures. However, capturing simultaneous radiographs from multiple angles requires large dedicated infrastructure, while asynchronous imaging introduces the problem of patient motion between scans. Much research has been devoted to providing simple and accurate calibration protocols, but the process remains difficult to translate to clinical practice.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in an embodiment, a method comprising: receiving a radiographic image dataset representing a sequential radiographic scan of a region of a human subject; receiving three-dimensional (3D) image data representing an optical scan of a surface of said region, wherein said 3D image data is performed simultaneously with said sequential radiographic scan; estimating a time-dependent motion of said subject during said acquisition, relative to a specified position, based, at least in part, on said 3D image data; and using said estimating to determine corrections for said radiographic image dataset, based, at least in part, on a known transformation between corresponding coordinate systems of said radiographic image dataset and said 3D image data.

There is further provided, in an embodiment, a system comprising: at least one hardware processor; and a non-transitory computer-readable storage medium having stored thereon program code, the program code executable by the at least one hardware processor to: receive a radiographic image dataset representing a sequential radiographic scan of a region of a human subject, receive three-dimensional (3D) image data representing an optical scan of a surface of said region, wherein said 3D image data is performed simultaneously with said sequential radiographic scan, estimate a time-dependent motion of said subject during said acquisition, relative to a specified position, based, at least in part, on said 3D image data, and use said estimating to determine corrections for said radiographic image dataset, based, at least in part, on a known transformation between corresponding coordinate systems of said radiographic image dataset and said 3D image data.

There is further provided, in an embodiment, a computer program product comprising a non-transitory computer-readable storage medium having program code embodied therewith, the program code executable by at least one hardware processor to: receive a radiographic image dataset representing a sequential radiographic scan of a region of a human subject; receive three-dimensional (3D) image data representing an optical scan of a surface of said region, wherein said 3D image data is performed simultaneously with said sequential radiographic scan; estimate a time-dependent motion of said subject during said acquisition, relative to a specified position, based, at least in part, on said 3D image data; and use said estimating to determine corrections for said radiographic image dataset, based, at least in part, on a known transformation between corresponding coordinate systems of said radiographic image dataset and said 3D image data.

In some embodiments, said radiographic image dataset is acquired using a slot-scanning method.

In some embodiments, said radiographic image dataset is acquired using a biplanar scanning method.

In some embodiments, said 3D image data comprises at least one of a point cloud, triangulated meshes, and splined surfaces.

In some embodiments, the method further comprises synchronizing, and the program instructions are further executable to synchronize, said optical scan with said radiographic scan in a time-dependent manner based, at least in part, on a known pixel sampling pitch of said radiographic scan.

In some embodiments, said motion comprises at least one of vertical motion, lateral motion, translational motion, and rotational motion.

There is also provided, in an embodiment, a method comprising: receiving a radiographic image dataset representing a sequential radiographic scan of said subject; receiving three-dimensional (3D) image data representing an optical scan of a surface of a human subject, wherein said optical scan is performed simultaneously with said radiographic scan; and calculating a transformation between respective coordinate systems of said radiographic and optical scans, based, at least in part, on known coordinates of a plurality of landmarks placed on said subject.

There is further provided, in an embodiment, a system comprising: at least one hardware processor; and a non-transitory computer-readable storage medium having stored thereon program code, the program code executable by the at least one hardware processor to: receive a radiographic image dataset representing a sequential radiographic scan of said subject, receive three-dimensional (3D) image data representing an optical scan of a surface of a human subject, wherein said optical scan is performed simultaneously with said radiographic scan, and calculate a transformation between respective coordinate systems of said radiographic and optical scans, based, at least in part, on known coordinates of a plurality of landmarks placed on said subject.

There is further provided, in an embodiment, a computer program product comprising a non-transitory computer-readable storage medium having program code embodied therewith, the program code executable by at least one hardware processor to: receive a radiographic image dataset representing a sequential radiographic scan of said subject, receive three-dimensional (3D) image data representing an optical scan of a surface of a human subject, wherein said optical scan is performed simultaneously with said radiographic scan, and calculate a transformation between respective coordinate systems of said radiographic and optical scans, based, at least in part, on known coordinates of a plurality of landmarks placed on said subject.

In some embodiments, the method further comprises synchronizing, and the program instructions are further executable to synchronize, said optical scan with said radiographic scan in a time-dependent manner based, at least in part, on a known pixel sampling pitch of said radiographic scan.

In some embodiments, the method comprises synchronizing, and the program instructions are further executable to synchronize, said optical scan with said radiographic scan in a time-dependent manner based, at least in part, on a known pixel sampling pitch of said radiographic scan.

In some embodiments, said radiographic image dataset is acquired using a slot-scanning method.

In some embodiments, said radiographic image dataset is acquired using a biplanar scanning method.

In some embodiments, said 3D image data comprises at least one of a point cloud, triangulated meshes, and splined surfaces.

In some embodiments, said landmarks are radio-opaque landmarks.

In addition to the exemplary aspects and embodiments described above, further aspects and embodiments will become apparent by reference to the figures and by study of the following detailed description

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
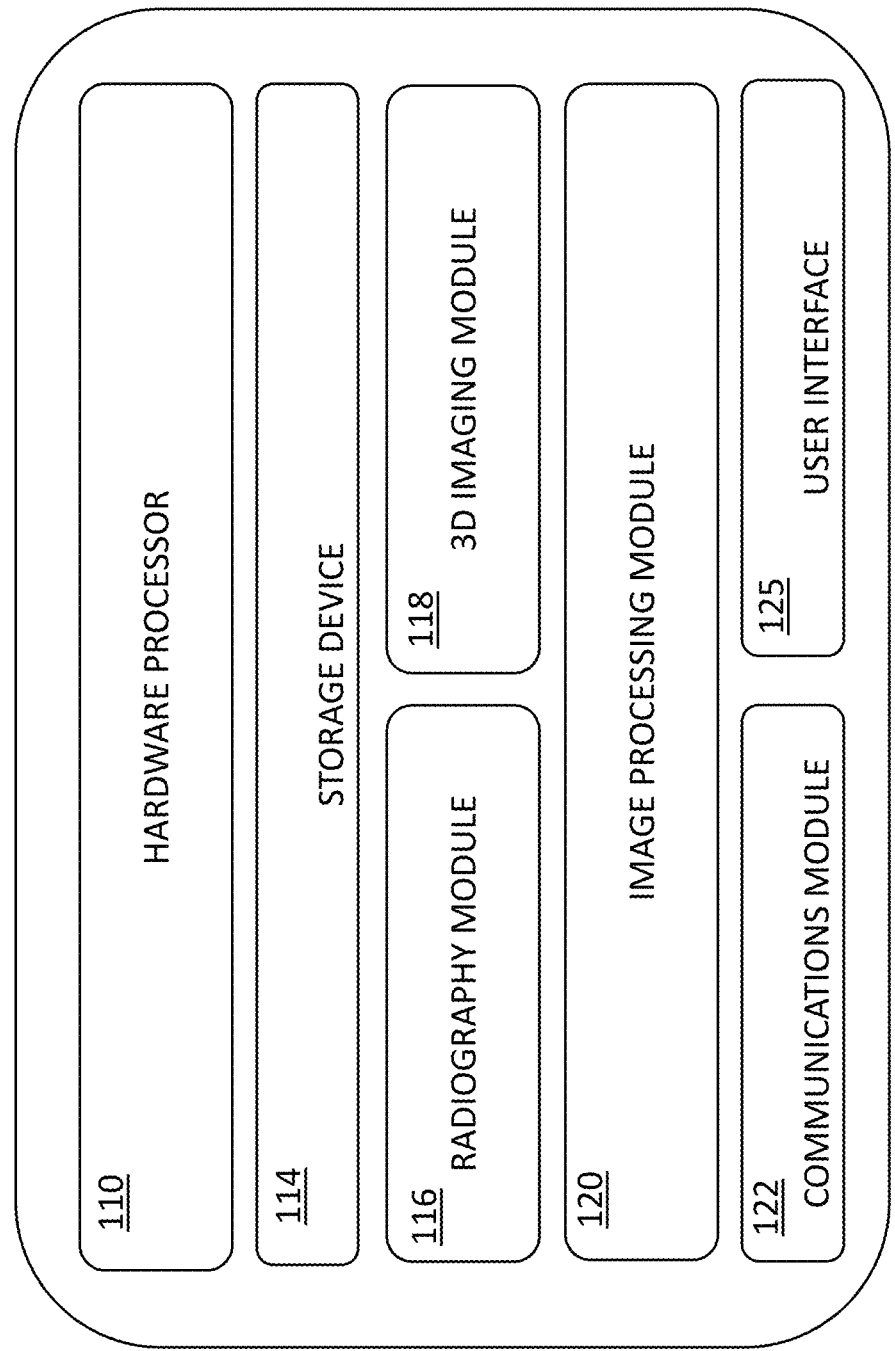
FIG. 1 shows a block diagram of an exemplary system, according to an embodiment of the present invention.

The present invention, in some embodiments, provides a system, method, and computer program product for correcting distortions in a radiographic scan image of an anatomical structure, wherein the distortions are caused by deviations of the subject being scanned from a desired posture during the scanning process.

In some embodiments, the present disclosure provides for modifying slot-scanned radiographic images post-hoc, using surface measurements of the subject recorded during the scan. Accordingly, translations in the radiographic image cause by subject movement can be corrected using concurrent surface recordings, to reduce motion artifact.

The present disclosure will focus on applications of the disclosed process in the context of bi-planar bodily scans in a standing position, specifically to detect spinal deformities (e.g., scoliosis). However, the present invention may be applied in connection with similar and/or other radiological scanning methods, including tomography, MRI, CT, enlarged radiography, stereo radiography, etc., and with respect to other anatomical regions and/or skeletal elements.

In some embodiments, the radiographic image may be produced by a radiography system which can be an x-ray system suitable for medical, industrial, and/or scientific applications. In some exemplary embodiments of the present invention, such an x-ray system can be designed to provide radiographic images by employing slot-shaped detectors and x-ray emitters designed to scan the vertical extent of a subject.

In some embodiments, the present disclosure provides for correcting radiographic images produced by x-ray systems, such as EOS, utilized to scan human bodies and generate images of anatomical structures in a three-dimensional fashion. In some embodiments, the imaging mechanism of EOS can be based on bi-planar slot scanners designed to capture x-ray beams scanning vertically the sagittal and the frontal planes of the subject.

The term "EOS" or "EOS Scan" refers to radiography system designed to provide frontal and lateral radiographic images, while limiting the X-ray dose absorbed by the patient in a sitting or standing position. In some embodiments, an EOS system can operate the bi-planar slot scanners in different angles. For example, a vertical scanning with a frontal view, as shown in FIG. 2B, can produce a radiographic image denoted as PA (posteroanterior) image, and a vertical scanning with a sagittal view can produce a radiographic image denoted as LAT (lateral) image. In some embodiments, the PA and LAT radiographic images can be utilized by the EOS to generate three-dimensional images of anatomical structure of the scanned subject.

In the bi-planar slot scanning, e.g., by EOS systems, each row of the PA image is collected simultaneously with the corresponding row of the LAT image. However, the X-ray emitters and the particle detectors must physically traverse the vertical extent of the patient from head to toe, a process which in some cases can take 10-25 seconds to complete. Patient movement during the scan results in characteristic wavy distortions on the image. Typically, people may naturally sway slightly when standing, but standing still is particularly difficult for younger patients. This motion can cause serious artifacts in radiographs, resulting in, e.g., the appearance of bowing in long bones of the lower extremities or lobular contours of internal organs.

Correcting motions in the scan using only the radiographic images presents several challenges. However, with access to prior information about the underlying motion that provoked the distortion, the problem becomes much more tractable. In this disclosure, a technique is proposed in which 3-dimensional (3D) scanning by, e.g., depth cameras, is performed during the radiographic scan, to measure patient motion directly, as elaborated further below.

In some embodiments, the process of detecting position changes of a body during the scanning operation of the EOS system can employ diverse techniques relying on external tracking of the subject motions performed simultaneously with the radiographic scanning process. In some embodiments, one or more depth cameras may be positioned to scan the surface of the body during the radiographic scanning.

In some embodiments, the present disclosure provides for imaging the subject and the position changes thereof during the scanning, wherein both imaging modalities, the radiographic and depth cameras, are aligned spatially and temporally. In some embodiments, the process of imaging a subject during a radiographic scanning produces a three-dimensional data set depicting the scanned subject during the scanning time.

Reference is made to FIG. 1 showing a block diagram of an exemplary system 100 according to an embodiment of the present invention. System 100 as described herein is only an exemplary embodiment of the present invention, and in practice may have more or fewer components than shown, may combine two or more of the components, or a may have a different configuration or arrangement of the components. The various components of system 100 may be implemented in hardware, software or a combination of both hardware and software. In various embodiments, system 100 may comprise a dedicated hardware device, or may form an addition to/or extension of an existing device.

In some embodiments, a computerized system, e.g., system 100, can be configured to receive radiographic images and 3D image data acquired during a radiography scanning, and process the received data set to detect position changes of the subject during the radiographic scanning, and translate these position changes into corrections of distortions in the radiographic scan.

System 100 may store in storage device 114 software instructions or components configured to operate a hardware processor 110 comprising one or more hardware processors (also "CPU," or simply "processor"). In some embodiments, the software components may include an operating system, including various software components and/or drivers for controlling and managing general system tasks (e.g., memory management, storage device control, power management, etc.) and facilitating communication between various hardware and software components.

In some embodiments, the software components of the system 100 may comprise an operating system, including various software components and/or drivers for controlling g and managing general system tasks (e.g., memory management, storage system control, power management, etc.) and facilitating communication between various hardware and software components.

In some embodiments, system 100 may comprise a hardware processor 110, a memory storage device 114, a radiography module 116, a 3D imaging module 118, an image processing module 120, a communications module 122, and a user interface 125.

In some embodiments, the radiography module 116 can be configured to receive bi-planar radiographic images acquired by a radiography system (not shown), which form the basis for a 3D reconstruction of the skeletal element (e.g., the spine). In some embodiments, the radiographic image data is the product of an EOS X-ray system, configured to simultaneously capture biplanar X-ray images by slot scanning of a whole body in an upright, physiological load-bearing position, using ultralow radiation doses. The simultaneous capture of spatially calibrated anteroposterior (AP) and lateral (LAT) images provides a 3D surface reconstruction of the skeletal system using a special software. Visualization of 3D reconstructed models in various views enables presentation of top view images to help analyze rotational conditions of lower limbs, as well as joints and spine deformities.

The radiography module 116 can also be configured to process the received radiographic images. In some embodiments, processing the received pixel data may comprise storing radiographic images in a storage device 114. In some embodiments, the radiography module 116 may be configured to communicate with the user interface 125 for the purpose of displaying the radiographic images to a user operating the system 100. In some embodiments, the user interface 125 may be configured to display the radiographic images.

In some embodiments, the radiography module 116 may be configured to perform one or more adjustments and/or processing steps with respect to the radiographic image data. Such processing may comprise presenting the radiographic images on a display device, changing the scale and/or the size of the radiographic images, aligning the radiographic images, and the like. In some embodiments, such instructions can be received from the storage device 114. In some embodiments, the instructions can be received from an input device, e.g., keyboard or a mouse input device, controlled by a user.

In some embodiments, the radiography module 116 may be configured to communicate with external computerized devices for the purpose of receiving radiographs from radiography systems. In some embodiments, the radiography module 116 may configured to communicate with digital storage mediums for the purpose of receiving radiographs.

In some embodiments, system 100 may operate the 3D imaging module 118 to receive 3D image data representing a body surface scan of human subjects. In some embodiments, the 3D image data can be received from a system designed to image at least some parts of a subject during a radiography scanning. In some embodiments, the system produces the 3D image data can employ depth cameras designed to the capture a 3D surface scan of a subject during the scanning time.

In some cases, the 3D imaging module 118 may be configured to represent the received 3D image data in a coordinate space, for the purpose of subject tracking. In some embodiments, such a coordinate space can be cartesian coordinates or angle-axis coordinates utilized to define the surface of the subject, as elaborated further below.

In some embodiments, system 100 may operate image processing module 120 for detecting the position changes of the subject in the 3D image data. The image processing module 120 may also be configured to transform the position change defined in the 3D image data to the radiographic images. In some embodiments, diverse computational methods and algorithms may be utilized to detect the pose defining the changes of the subject in the 3D image data. In some embodiments, the image processing module 120 may be configured to align the radiographic images and the 3D image data spatially and temporally for the purpose of converting the movements detected at the objects in the 3D image data into changes at the radiographic images. In some embodiments, image processing module 120 may be configured to communicate with the radiography module 116 for obtaining the data of the radiographic images and calibrate the obtained radiographic image with obtained 3D image data.

In some embodiments, image processing module 120 may utilize the storage device 114 for storing data required during the processes managed by these modules. In some embodiments, storage device 114 may be coupled to the hardware processor 110 in order to utilize the hardware processor 110 in the image data processing.

In some embodiments, system 100 may utilize storage device 114 for storing the corrected radiographic images. In some embodiments, system 100 may allow access to storage device 114 to a third-party device, or any other extremal computerized device. In some embodiments, a radiography system, e.g., EOS can access storage device 114 to receive the corrected radiographic images. For example, an EOS can access storage device 114, copy corrected PA and LAT radiographic images and reconstruct a three-directional image of at least one corrected anatomical structure.

In some embodiments, the process of converting the detected position changes of a subject in the 3D image data, to distortions in the radiographic images may require a calibration process between both imaging modalities, the radiographic and depth cameras. In some embodiments, the calibration with EOS may be performed by first scanning a target whose position can be accurately measured with both surface scans and radiographic imaging. In some embodiments, this target can be scanned both with EOS and the depth cameras and the position determined of this target can be defined in each coordinate system. In some embodiments, the process of converting the detected position changes of a subject in the 3D image data, to distortions in the radiographic images may also require a synchronization between surface scanning performed by the depth cameras and radiographic scanning.

Figure 2A:
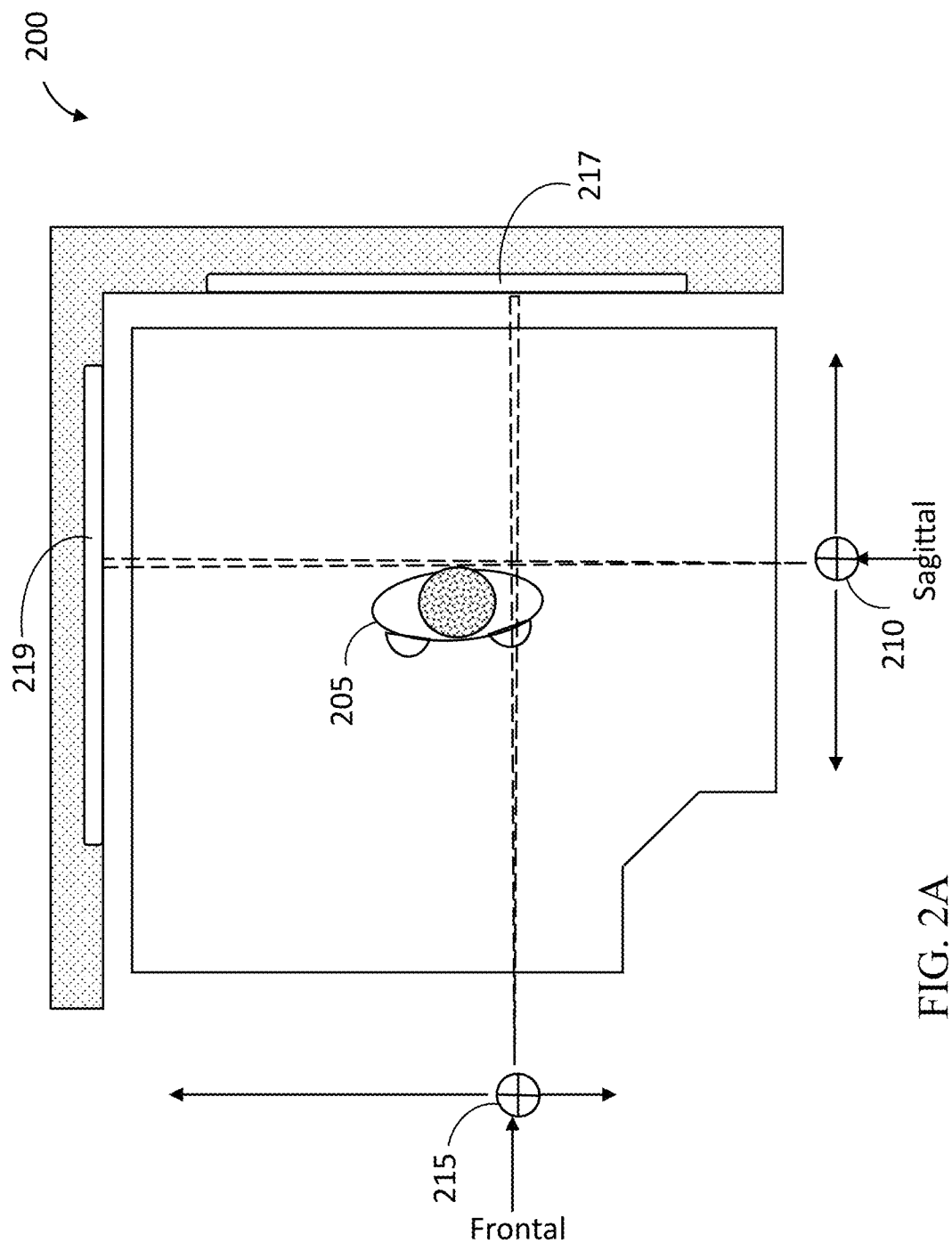
FIG. 2A shows a schematic structure of a slot-shaped scanner.
Figure 2B:
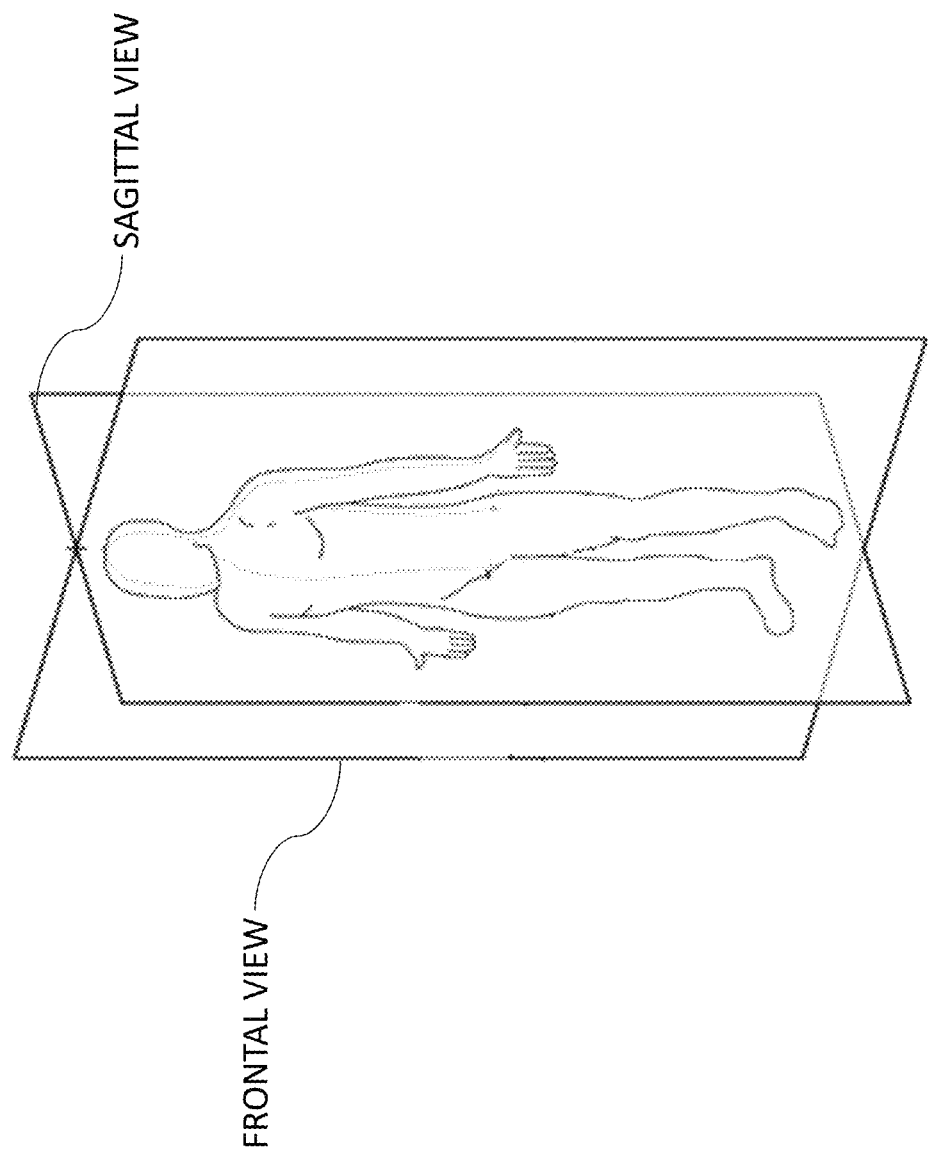
FIG. 2B shows a frontal (PA) and Sagittal (LAT) view of a subject, according to some embodiments of the present invention.

Reference is made to FIG. 2A showing a schematic structure of slot-shaped detectors and x-ray emitters designed to scan an object vertically, according to exemplary embodiments of the present invention.

Radiographic slot scanners produce high contrast images with minimal ionizing radiation, but suffer from increased susceptibility to motion artifact during extended scan times. In some embodiments, the present disclosure can present a motion correction technique relying on external tracking of patient position via simultaneous surface scans. Depth cameras are mounted to a bi-planar slot scanner and are spatially and temporally synchronized to the radiographic environment. Patient motion is tracked by fitting a surface model to these depth scans, and radiographic images are modified post-hoc to rectify motion-induced distortion. In some cases, simulations of patient movement during scanning show a 77% reduction in landmark reconstruction error, while experiments carried out at the Hospital for Special Surgery show a 44% error reduction. The proposed technique is empirically validated in the context of standing slot scans and offers a means of objectively measuring patient movement and the resulting effect on scanned anatomical structures.

FIG. 2A shows a schematic configuration of an EOS 200 comprising radiographic slot detector designed capture radiographs simultaneously from more than one angle. The EOS 200 can allow scanning a patient 205 simultaneously by x-ray emitters 215 providing the PA scanning (shown in FIG. 2B) and the x-ray emitters 210 providing the LAT scanning (shown in FIG. 2B).

In some embodiments, the EOS 200 can also comprise a slot-shaped detector 217 configured to capture the x-ray beam received from the x-ray emitter 215, and a slot-shaped detector 215 configured to capture the x-ray beam received from the x-ray emitter 215, wherein each line of the radiographic image captured by each of the slot-shaped detectors, is collected sequentially and converted to a pixel row.

In some embodiments, the scanning process can be performed while the beams of the x-ray emitters impinge the slot-shaped detectors and deriving pixel values related to x-rays received during respective time frames. In some embodiments, the structure of a radiographic image resulting from such scanning can comprise pixel positions arranged in N number of rows and M number of columns.

In some embodiments, a scanning conducted by EOS 200 produce a PA image and a LAT image which can be used to construct a three-dimensional structure of at least a part of the anatomical structure of the scanned subject.

In some exemplary embodiments, the EOS 200 can be configured such that, each row of the PA image is collected simultaneously with the corresponding row of the LAT image. In some cases, at the scanning process the x-ray emitters and the slot-shaped detectors physically traverse the vertical extent of the subject from head to toe. In some embodiments, the EOS 200 can be configured to associate a time window (denoted herein by W) with radiography scanning process.

Stereo radiography fills an important niche between planar radiography and computed tomography, allowing analysis of skeletal structure in load bearing posture. Although stereo images do not provide true three-dimensional measurements, stereo-reconstruction allows for 3D analysis of targeted structures. However, capturing simultaneous radiographs from multiple angles requires large dedicated infrastructure, while asynchronous imaging introduces the problem of patient motion between scans. Much research has been devoted to providing simple and accurate calibration protocols, but the process remains difficult to translate to clinical practice.

One exemplary system of radiographic scanner can be the EOS system, which provides hardware calibrated low-dose high contrast full-subject biplanar images in standing. However, the hardware of this exemplary solution introduces a problem not faced by traditional X-rays, as patient motion can easily distort the radiograph.

Radiographic slot scanners (e.g., DXA or EOS systems) can produce high contrast planar images with comparatively low doses of ionizing radiation. These scanners expose and record one image row at a time, in contrast with traditional X-ray machines where the entire image is captured simultaneously. This inherently imbues slot imaging systems with an improved signal-to-noise ratio, as x-rays that are deflected off the imaging line are ignored rather than contributing to noise.

In such systems, each line of the radiographic image is collected sequentially. For example, in the EOS-based systems, each row of the frontal image, also known as PA image, can be collected simultaneously with the corresponding row of the sagittal image, also known as LAT image. In cases where a slot scanner is employed, each line of the radiographic image is collected sequentially. For example, in current EOS systems, each row of the PA image is collected simultaneously with the corresponding row of the LAT image.

However, in some cases, the advantages of slot scanners come at the cost of increased susceptibility to motion artifact, as the X-ray emitter is mounted to a gantry or track that must traverse the radiographic subject. Thus, the present disclosure can be used to operate in the context of the EOS system, a biplanar slot scanner for standing posture. EOS scans take 5-30 s, depending on patient height and scan protocol, during which time any movement of the patient may be recorded as distortions in the radiographic image. Even healthy adult subjects have a natural sway frequency when standing, while pathological subjects may exhibit perturbed sway patterns. Nearly 20% of instrumented scoliosis patients show obvious motion artifact, while EOS scanning may be contraindicated entirely for very young children (younger than 7 years) due to their difficulty standing still.

Experimental Setup and Techniques
Experimental Human Torso Model

Figure 3A:
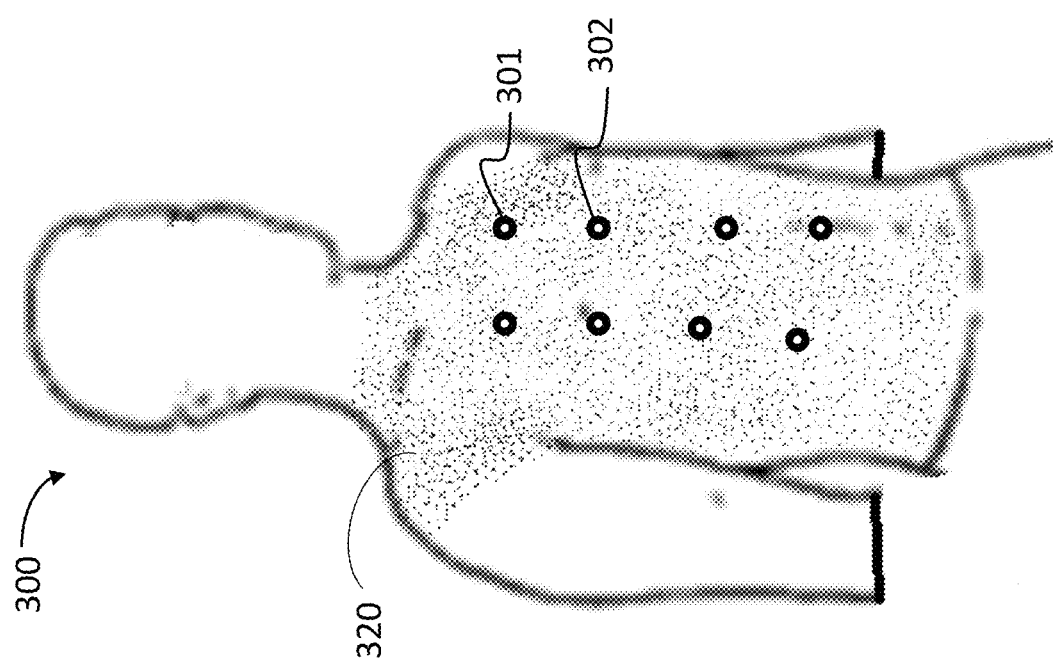
FIG. 3A shows an emulated 'phantom' human subject, according to some embodiments of the present invention.
Figure 3B:
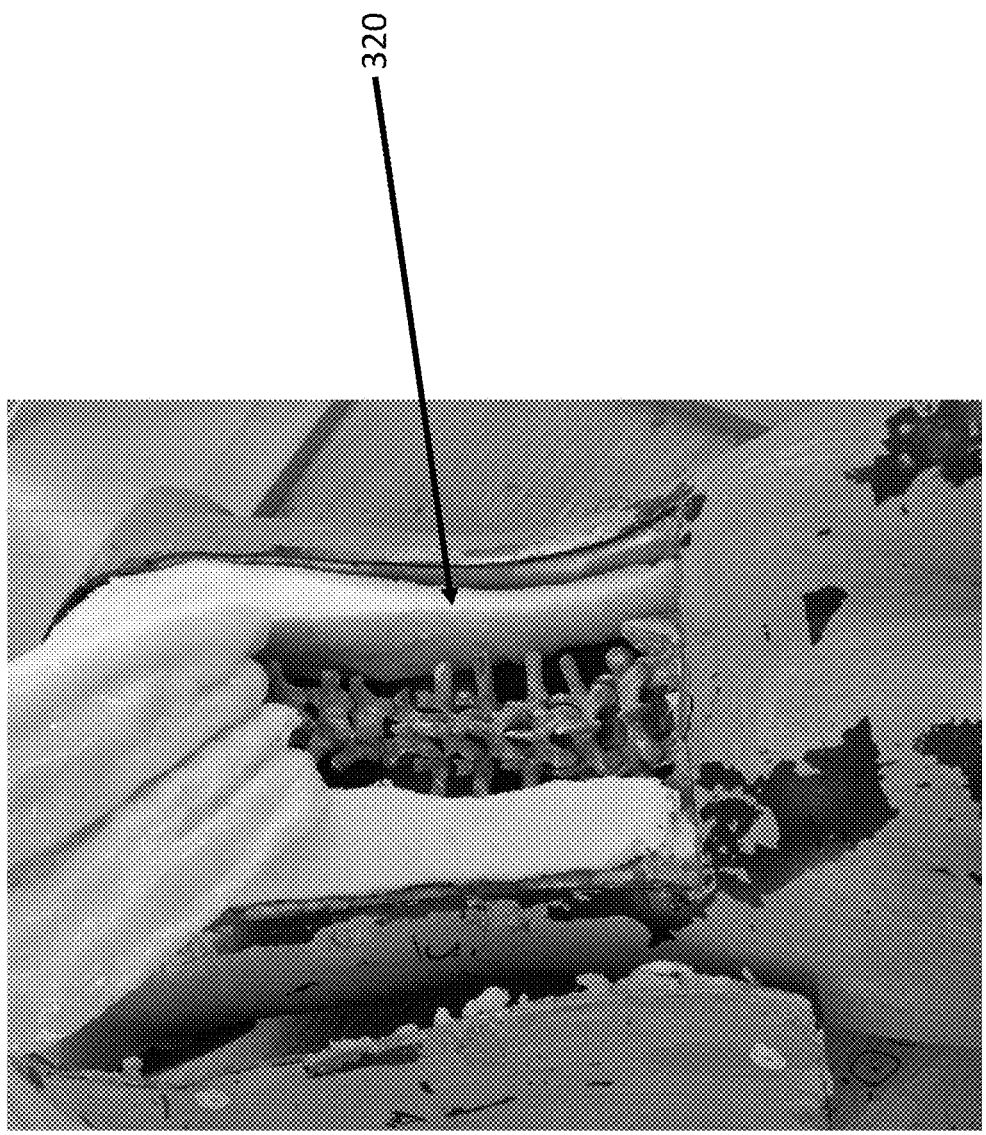
FIG. 3B shows an embedded radiographic spine model, according to some embodiments of the present invention.

With reference to FIG. 3A, in some embodiments, an emulated 'phantom' human subject can be constructed by embedding a radiographic spine model (e.g., C1 to sacrum, Sawbones, Malmo, Sweden) inside a rigid torso model (e.g. torso of subject 300) and secured in place with tightly packed foam (Torso 320 in FIG. 3B). Additionally, a plurality of radiopaque spherical markers (e.g., 16 markers) can be embedded in the surface of the subject similar to the torso in order to allow unambiguous stereo reconstruction of the position and orientation of the phantom.

After sealing the surface with glue (e.g., epoxy), the subject can be scanned with a state-of-the-art photogrammetry system (3dMD, Atlanta, GA, USA) that generates a surface mesh of the scan subject with sub millimeter accuracy. Such a subject can be scanned with CT and the radiopaque markers, which in some cases can be manually labeled. CT voxels above threshold can be identified and the subject surface can be converted to a cloud of points that was then registered to the aforementioned surface mesh from 3dMD using a point-to-surface Iterative Closest Point (ICP) algorithm.

In some embodiments, the final result is a high-accuracy surface mesh (e.g., 72613 vertices, 133025 faces can be identified) with 16 landmarks in the same coordinate system.

Intermodal Calibration

Figure 4:
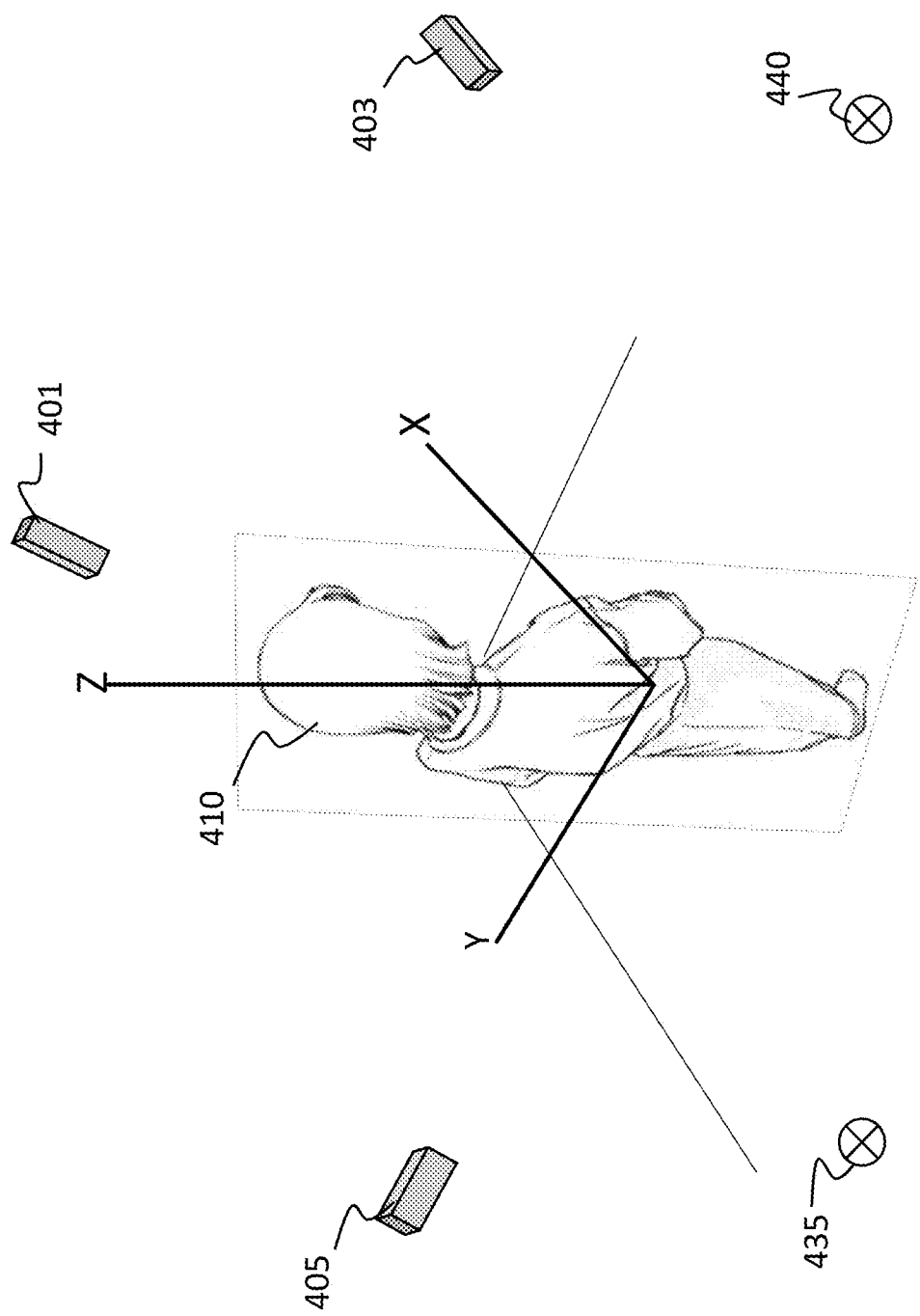
FIG. 4 shows a three depth cameras layout, in accordance with some embodiments of the present invention.

Reference is made to FIG. 4, showing three depth cameras layout, in accordance with some embodiments of the present invention. FIG. 4 shows depth cameras 401, 403, 405 which can be coordinated with, e.g., EOS 200 in FIG. 2A to provide the external scanning of the subject 410.

In some embodiments, depth cameras 401, 403, 405 can be characterized with relatively long depth of field, e.g., between 0.16 and 10 meters, high sensor resolution, e.g., 1920×1080, and high frame rate, e.g., 90 FPS, to allow depth perceptions capabilities.

In some embodiments, the depth cameras 401, 403, 405 can be connected to a dedicated image processing unit (not shown) configured to utilize the depth cameras to generate a 3D image data of the subject 410.

In some embodiments, the layout of the depth cameras 401, 403, 405 is optimized for the origin of the axes, wherein the origin of the axes is the iscomeer of the radiography system (e.g., as shown at FIG. 4 iscomenter 427).

In some embodiments, the various three-dimensional graphic techniques can used to represent geometric data required for generating the 3D image data depicting the subject 410. In some embodiments, computer techniques based on surface mesh can be employed to generate the required 3D image data depicting the subject 410.

In some embodiments, the depth cameras 401, 403, and 405 (for example three Intel Real Sense D435 cameras) can be placed around a radiographic center of the EOS area (e.g., as shown at FIG. 4) and controlled by a custom multi-threaded application.

In some embodiments, relative positions between each camera can be calculated by moving a spherical calibration target through the mutually visible area and finding the center of the sphere in the local coordinate system of each camera. In some embodiments, the sphere centers can be then registered to a single coordinate space, e.g., by using singular value decomposition (SVD). In some embodiments, where all cameras are mutually calibrated, the depth outputs can be merged into a single point cloud stream (e.g., cloud point stream collected at 30 fps). In some cases, each camera captures depth and color images at 30 fps and records the data as a point cloud, along with a timestamp, as elaborated further blow.

In some embodiments, the precise geometry of the X-ray emitter and detector are known and indicated in the output DICOM files.

In some embodiments, the projection from 3D world coordinates (x, y, z) to PA (also known as the frontal) image coordinates (u, v) in an image of M×N pixels, where M is the number of columns and N is the number of rows is given as:

$$\begin{bmatrix} u_c \\ v_c \end{bmatrix} = \begin{bmatrix} M_c - \quad z/p \\ \frac{N_c}{2} - \frac{f_c y}{P(x+f_c)} \end{bmatrix} \quad (1)$$

$$\begin{bmatrix} u_s \\ v_s \end{bmatrix} = \begin{bmatrix} M_s - \quad z/p \\ \frac{N_s}{2} - \frac{f_s x}{P(y+f_s)} \end{bmatrix} \quad (2)$$

wherein p is the sampling pitch and f is the distance from the emitter to the radiographic image plane. Subscript c in indicates coronal (PA) while s indicates LAT image. By convention, the origin is taken as the radiographic center at floor level, the X and Y axes can be directed towards the PA and LAT detectors, respectively, while the Z axis is oriented vertically, as shown in FIG. 4.

In some embodiments, to find the transformation between depth camera coordinates and the EOS coordinate system, a calibration target is required to be located in each modality the EOS and the depth cameras.

In the present experimental setup, the 'phantom' torso model may be used for this purpose. In some embodiments, manually labeled stereo-corresponding points can be reconstructed in 3D by jointly solving Eqs. 1 and 2 above for (x, y, z).

In some embodiments, a number of radiopaque markers may be placed on the subject 410 for the purpose of registering the subject 410 to the surface mesh model of the subject 410. An exemplary case can be shown in FIG. 3A which shows a subject 300 with 16 radiopaque landmarks, e.g., eight radiopaque landmarks in the front (e.g., markers 301, and 302), and eight radiopaque landmarks in the back (not shown). In some embodiments, the process of utilizing radiopaque markers can be utilized for associating between the subject 410 and the surface mesh model.

To perform the calibration, the subject can be stably positioned at the radiographic center and simultaneously scanned with both EOS and depth cameras. The resulting point cloud can then be filtered by color and registered to the torso surface mesh from 3dMD. Finally, registration to EOS space can be performed by finding the rigid transform of the 16 radiopaque landmarks to the reconstructed EOS markers using, e.g., SVD. The result is a registration from unified depth camera coordinates to EOS coordinates. The subject can be moved slightly, and the process repeated a total of three times and the results averaged.

FIG. 4 also shows the X-Ray emitter 435 configured to provide the PA scanning and the X-Ray emitter 440 designed to provide the LAT scanning.

In some embodiments, a metal pole (not shown) can be attached to the patient 410. Such a metal pole can be used as a mechanical clock, visible in both imaging modalities, the radiographic with X-Ray emitter 435 and 440, and the depth cameras 401, 403, and 405.

In some embodiments, identifying the synchronization between the 3D image data and radiographic image a use of the LED indicators seen by the x-ray emitters can be made. In some embodiments, the position of the X-ray emitter can be directly measured by attaching photocells to the external paneling of the scanner.

In some embodiments, the LED indicators can be configured such that during an EOS scan the LEDs move past the photocells, eliciting a spike in voltage that provides the temporal correspondence between images of the depth camera and radiographic image row. Timestamps for the remaining rows in the image can be extrapolated using the speed of the EOS scan.

Imaging Motion Tracking and Correction

In some embodiments, a subject may be scanned by a temporally-aligned combination of a radiographic scan and an optical scan. In some embodiments, the scan may be provided by a combination of, e.g., an EOS radiography system and a depth camera array. In some embodiments, the EOS radiography system may produce, e.g., PA and LAT radiographic images. In some embodiments, the combined scan may produce radiographic image dataset representing a sequential scan of a region of the subject, as well as a 3D image data representing a scan of a surface of that region. In some cases, the radiography scan produced a pair of radiographs (PA and LAT), wherein the 3D surface scan may produce, e.g., a 330-point cloud.

In some embodiments, wherein surface mesh technology is used, for each point cloud, the subject surface mesh can be registered with point-to-surface ICP and the center of mass (CoM) of the mesh vertices can be computed.

In some embodiments, calibration step is performed. In some embodiments, in order to integrate surface information with radiography, both imaging modalities, the radiographic and depth cameras, may be aligned spatially and temporally.

For temporal synchronization, this disclosure provides for a mechanical device to synchronize an external computer with the radiography system. By including a radiopaque mechanism with known motion in the radiographic FoV, it can be possible to compute the instant at which each row of the radiographs can be recorded, with reference to an external computer. In some cases, a spatial calibration is performed by imaging a calibration target that can be unambiguously located in both depth images and radiographs.

Furthermore, the average CoM across the entire scanning can be computed as a single point in 3D space. In some embodiments, the next step can be to synchronize the surface mesh and the radiographic image temporally, as they were collected on different machines and do not share a clock, visible in both radiographic and depth modalities.

Figure 6:
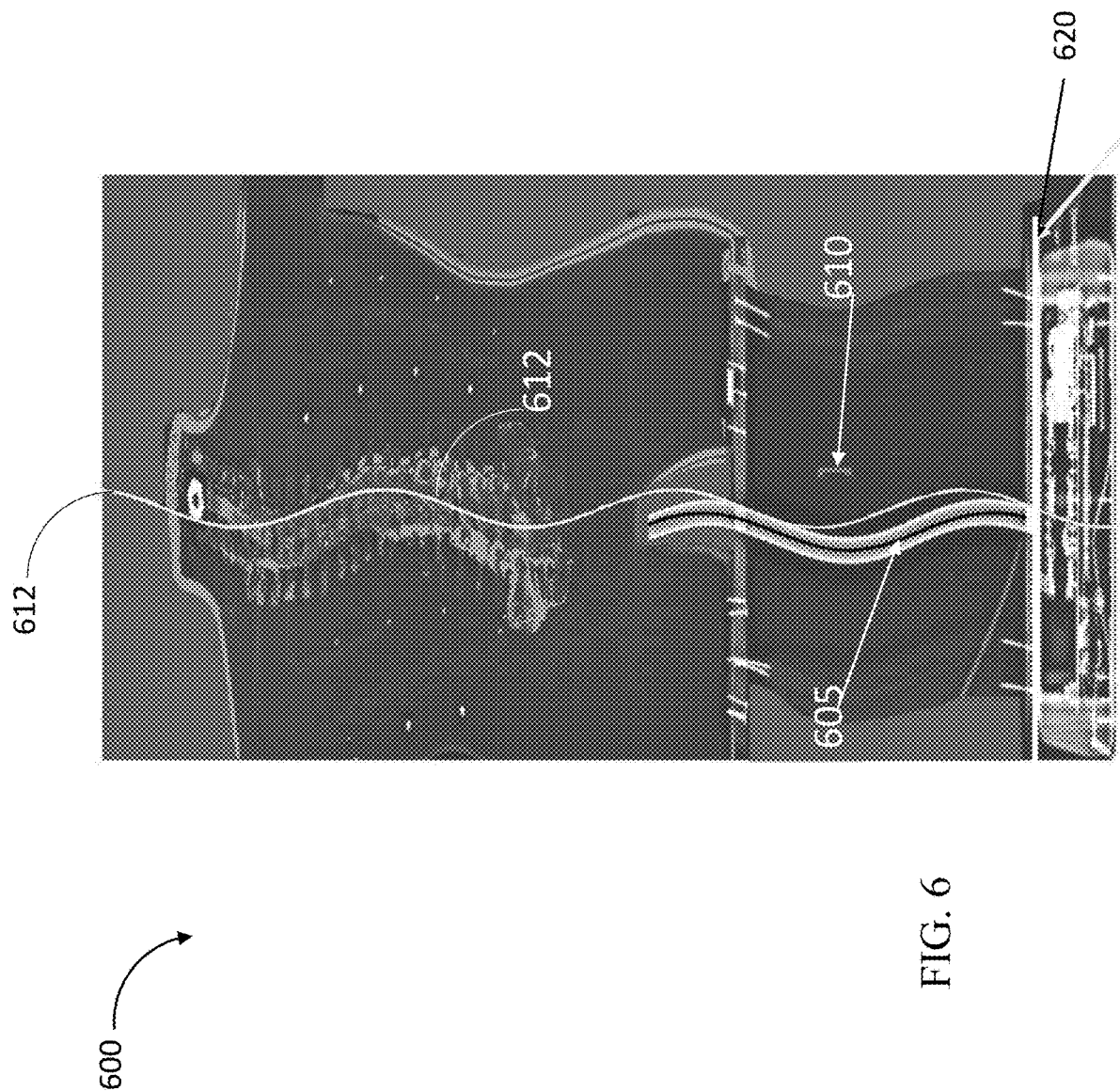
FIG. 6 shows a radiograph depicting an anatomical structure imaged with synchronization between radiographic images and depth camera, according to some embodiments of the present invention.

In some embodiments, for both PA and LAT radiographs, a sinusoid can be fitted to the center of the metal pole, clearly visible in the support structure (the curve 605 in FIG. 6). Likewise, the average CoM can be plotted against time and a sinusoid fitted to horizontal displacement. Then the average CoM can be projected onto each radiograph according to:

$$\begin{bmatrix} u \\ v \end{bmatrix} = \begin{bmatrix} A \cdot \sin\left(\frac{2\pi t}{\lambda} + \phi\right) + b \\ Mt/D \end{bmatrix}, \quad (3)$$

where A is the amplitude of lateral motion, b is the mean position, λ is the period in seconds, t is the time since the start of the recording, and D is the scan duration. Synchronization is performed by finding the offset (offset 610 at FIG. 6) between the two sinusoids to minimize the sum of squared differences in relevant vertical range.

In some embodiments, the physical dimensions of the scanner impose severe constraints on placement when adding optical scanners to the EOS. As a consequence, it can be challenging to collect partial scans with even half of the subject in the field of view. In some cases, to overcome this, a pre-determined surface model of the subject is fitted to the partial point clouds produced by depth cameras. The center of mass of the model can be calculated for each point cloud, and the horizontal displacement of this point can be projected onto each radiographic image plane.

In some other embodiments, to perform a motion correction, a single reference pose must be selected. In some other embodiments, a different coordinate system may be selected, e.g., the reference pose can be defined by using angle-axis formulation, as further elaborated below.

In some embodiments, image motion correction can be managed by the computerized system 100. In some embodiments, simple motion correction can be performed by shifting each row of the radiograph according to the measured displacement of the imaged subject. According to Eq 3, after synchronization each image row corresponds to a point in time.

Accordingly, in some embodiments, analyzing image data, such as 3D image data to detect motions of a subject, utilize this image data to identify the distortions and rectify them in the radiographic image may be accomplish by a protocol which essentially comprises the following basic steps:

Imaging the subject, simultaneously by both imaging modalities, the radiographic and depth cameras.

Align image data obtained from both imaging modalities spatially and temporally.

In the image data obtained from the depth cameras, define a single reference point in 3D space defining the motion of the subject during the scanning time Represent the single reference point in a coordinate space of the radiographic images, e.g., in an array of N rows and M columns.

Rectify the distortions of the radiographic images through shifting the row horizontally, according to the motions depicted by the single reference point.

In some embodiments, aligning the imaging modalities may require prior alignments of the modalities. For example, such by alignments may be using point clouds intensity of a CT scan with radiopaque markers.

In some embodiments, the lateral displacement of the subject at that moment is found by subtracting the average CoM (described above) from the instantaneous CoM. This displacement, projected onto the horizontal axis of the image plane, corresponds to the movement of the subject relative to the average position. Motion correction is performed by simply shifting the entire row to counteract this lateral motion. The process is repeated for each row of every image.

Figure 7:
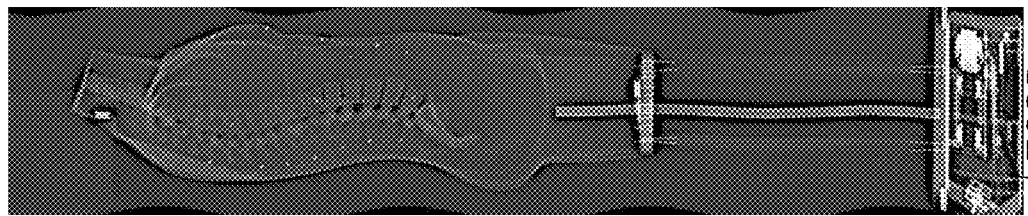
FIGS. 7-8 show visual results of the methods disclosed herein, according to some embodiments of the present invention.
Figure 7:
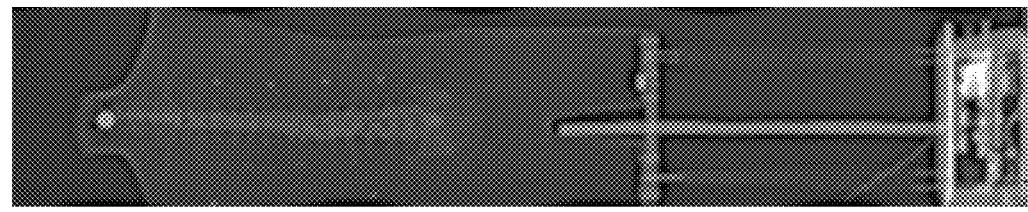
Figure 7:
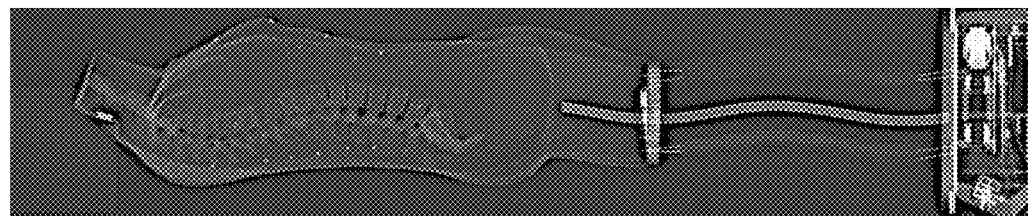
Figure 7:
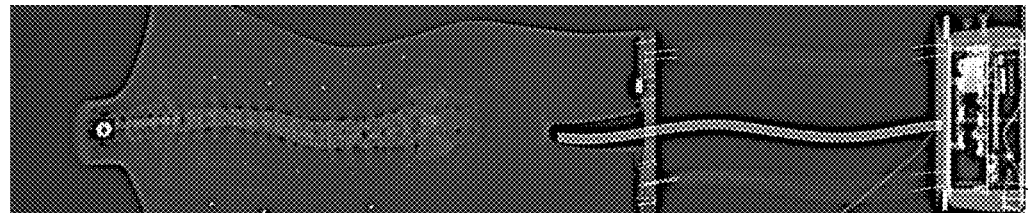

The visual results demonstrate clearly that the protocol is effective for this experimental setup (e.g., as shown in FIG. 7). This study acts as a proof of concept for slot scanner motion correction. The key innovation is to integrate another modality to directly measure patient motion during the scan. This information can then be used to adjust the radiographs post hoc. There are fundamentally three stages in this process.

In some embodiments, a synchronization between the depth camera and the radiographic image can provide a unique timestamp for each row of the radiographic image. The subject's displacement for each row is interpolated from the motion computed from the optical scans. Image correction is performed by shifting each row to compensate for the lateral motion. In principle this technique can be applied not only to radiography systems, but any line scanner. For example, a high-accuracy LIDAR line scanner could be supplemented with a fast full-frame optical scanner (e.g. depth camera) to perform motion correction on a moving target (e.g. human subject).

Motion Correction Via Depth Imaging

In some embodiments, the present disclosure provides for an intermodal motion correction method targeted at standing slot radiography, using stereo depth cameras to track subject motion. These methods are tested in computer simulations as well as in "in vitro" experiments using a radiographic phantom. In some embodiments, the present disclosure provides means to objectively measure patient movement in 'un-instrumented' patients, which may provide valuable insight into the true extent of motion observed in clinical scans.

Figure 5:
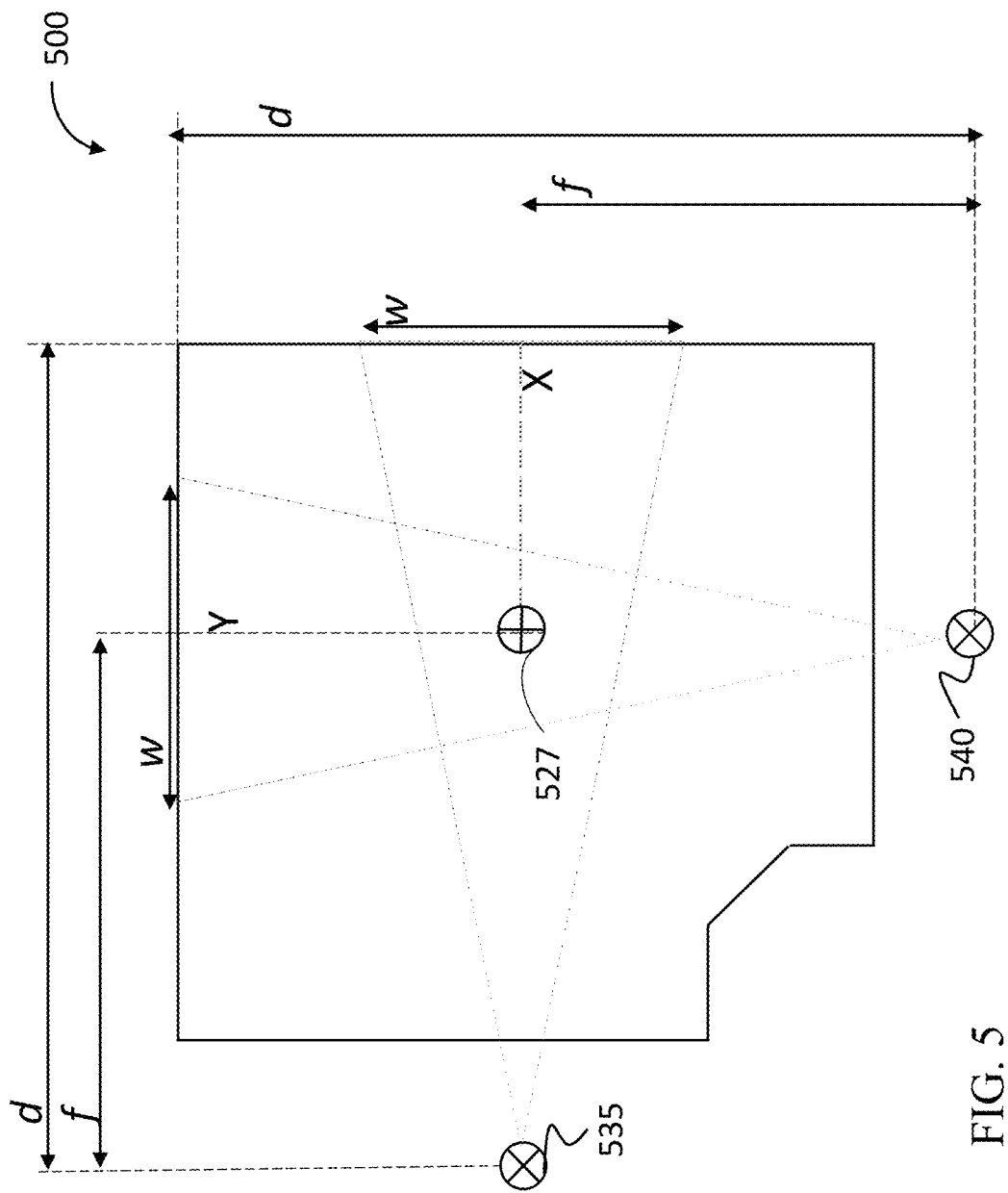
FIG. 5 illustrates an upper view of an EOS system with depth cameras utilizing angle-axis, in accordance with some embodiments of the present invention.

FIG. 5 illustrates an upper view of a scanning system configured to a biplanar radiographic scan of a subject, while recording subject position for the duration of the radiographic scan. With subject motion known and registered to the EOS environment, it is possible to modify radiographic images post-hoc to generate a motion-corrected scan.

FIG. 5 illustrates an optional setting of the two modalities, the 3D cameras and the radiography scanning. Such a setting may allow calibrating the two modalities by utilizing angle-axis. In some embodiments, a collaboration in the angle-axis as illustrated herein can be utilized in the imaging, motion tracking and correction steps as elaborated above.

FIG. 4 shows scanning system 400 with slot emitters 435 configured to provide the PA scanning and 440 configured to provide the LAT scanning. FIG. 4 also defines the distance d between the emitter and the detector, the distance f between the emitter and the isocenter 427 and the time W of a row scanning.

In some embodiments, the structure provided here can be utilized for optimizing the structure of the EOS at the isocenter, such that the row-shift algorithm essentially translates each image row such that the central image column is at the isocenter 427.

In some embodiments, global coordinates can be defined according to the global axis system as defined by the Scoliosis Research Society (SRS). In some embodiments, a single reference can be set according to a subject placed at the isocenter 427 with axes directed anterior (x), left (y), and cephalad (z) relative to patient positioning. In some embodiments, pixel coordinates for radiographic images can be indexed from the top left corner relative to the slot emitter 440, according to radiographic convention (e.g. patient left shown on image right for a posterior-anterior (PA) scan).

To perform motion correction, a single reference pose may be selected. In some cases, for a rigid-subject movement is assumed, parameterized as a 6-element twist vector:

$$\vec{T}(t) = \langle \omega(t), \delta(t) \rangle \quad (4)$$

with corresponding transformation matrix T(t), relative to the initial position as a function of time t. The reference pose is defined as the average translation (transformation) and rotation using angle-axis formulation:

$$\vec{\mu} \equiv \arg\min_{\vec{T} \in \mathbb{R}^6} \sum_i d(\vec{T}, \vec{T}_i) \quad (5)$$

Here distance d between two rigid transforms is given by:

$$T_{2,1} = T_2^{-1} \circ T_1 \quad (6)$$

$$d(\vec{T}_1, \text{vec}T_2) = \|\omega_{2,1}\|^2 + \|\lambda \delta_{2,1}\|^2 \quad (7)$$

wherein $T^{-1}$ is the inverse of transform T and the $\circ$ is an operation which concatenates subsequent transformations. Using standard SI units, a $\lambda=1$ is set since rotation and translation (transformation) components are in the same order of magnitude.

In some embodiments, a slot emitter can move at a constant rate, providing time t as a linear function of image row r and vice versa. Therefor transformations from the mean pose to scanned position can alternatively be parameterized by row.

In some cases, with a simplified case of rigid subject motion, perfect image restoration is generally impossible. Rotation about the vertical axis, for example, causes parallax effects that cannot be resolved by image warping, as each pixel corresponds to a line segment passing through the imaging subject.

In some embodiments, as an approximation, the scan subject can be treated as a two-dimensional structure parallel to the imaging plane, located at the isocenter 427. For a frontal image (PA), for example, the subject can be considered to lie on the y, z plane with x=0.

In some embodiments, two methods of image modification may be employed: nonlinear warp fields (WF), and horizontal row shifts (RS).

Warp Field

In the wrap field, for each pixel <u, v> in the target image, the process can be defined as: Find the corresponding position P in global coordinates by scaling by the pixel pitch π. For a PA image:

$$P = \begin{bmatrix} x \\ y \\ z \end{bmatrix} = \begin{bmatrix} 0 \\ \pi\left(u - \dfrac{c}{2}\right) \\ z_0 - \pi v \end{bmatrix} \quad (8)$$

wherein c is the final column index and $Z_0$ is the height of the first row. Then, Eq. 6 is applied to find the corresponding point P'(t) on the scanned target as a function of time. Then, for the given point trajectory, the time t* is defined such that $z'=Z_0-\pi r(t)$ which is at the point in time when the scan point is intersected by the scan beam. Then project this point P* back into radiographic image space:

$$\begin{bmatrix} u^* \\ v^* \end{bmatrix} = \begin{bmatrix} \dfrac{c}{2} + \dfrac{y^* f}{\pi(f + x^*)} \\ (z_0 - z^*)/\pi \end{bmatrix} \quad (9)$$

where f is the distance from emitter to isocenter 427. The difference ⟨u*, v*⟩−⟨u, v⟩ determines the deformation that must be applied to the radiographic image. The same procedure is repeated for the LAT image.

Row Shift

In some embodiments, for the row shift, as a further simplification, subject movement can be modeled as pure translation on the axial plane by neglecting rotation and vertical motion. In this case image correction at step 420 can be performed simply by shifting rows laterally, counter to recorded movement. This may be a reasonable simplification in the case of standing scans. In some cases, wherein the patient is modeled as an inverted pendulum, the small angle approximation yields predominantly lateral movement.

In some embodiments, to perform Row Shift image correction, the horizontal component of the Warp Field at the isocenter 427 (at x=0, y=0) may apply to each row of the image. In other words, discount any change in the z direction and apply a uniform column shift $u^*-u|_{x,y=0}$ to the entire row.

Reference is made to FIG. 6 showing a radiograph depicting an anatomical structure imaged with synchronization between radiographic images and depth camera, according to some embodiments of the present invention. FIG. 6 shows a radiograph 600 with a sinusoid 605 fitted to the vertical metal bar 620 as seen in the radiograph. Radiograph 600 also comprises a sinusoid 612 fitted to torso position and projected onto the radiographic. Radiograph 600 also comprises a mark 610 reprinting the difference in phase corresponds to the temporal offset between both imaging modalities, the radiographic and depth cameras. In FIG. 6, the aspect ratio in the radiograph is adjusted to emphasize fitted curves.

In some embodiments, at the imaging steps, the subject (torso with embedded spine) can be mounted a wooden support structure and then affixed to a variable speed rotating platform with a radius of rotation of 1 cm (e.g., MRC ltd. DOR-2828). In addition, a straight metal tube can be installed vertically in the wooden support structure. The subject was placed at radiography system (e.g., EOS) center and the rotating table set to approximately ⅓ Hz. The radiography system scans can be performed with peak voltage of 80 Kv, current of 250 mA, taking 11.08 s to traverse a vertical Field of View (FoV) of 1.675 m. Simultaneous with radiography, depth cameras recorded unified point clouds at 30 fps in the 3D radiography system coordinate frame, as aforementioned.

The key innovation is to integrate another modality to directly measure patient motion during the scan. This information can then be used to adjust the radiographs post hoc, while the basic protocol comprising collaborating, imaging and tracking, and corrections are kept.

FIG. 7 illustrates the effect of motion correction according to the protocol mention above, wherein row PA image is depicted by image 701A and the row LAT image is depicted by image 702A. FIG. 7 also illustrates the corrected images wherein the corrected PA is depicted by image 701B and the corrected LAT is depicted by image 702B.

Figure 8:
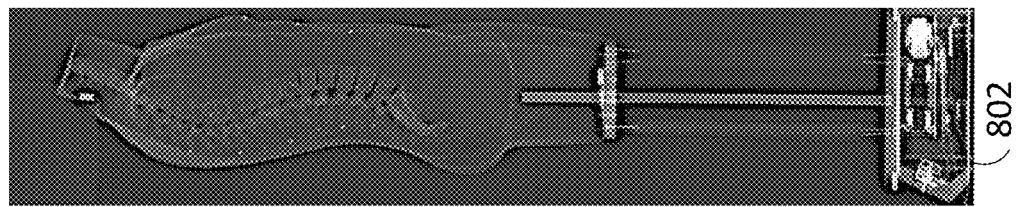
Figure 8:
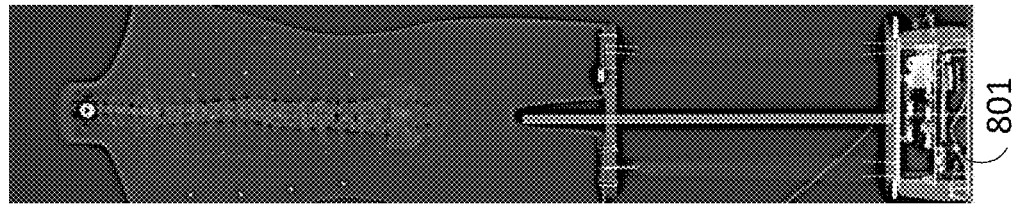

The LAT and PA views can be compared with the static scans shown for references in FIG. 8, wherein images 801 and 802 depict views of a static subject.

In some embodiments, particular usage can rely on the D435 depth cameras from Intel. In some other embodiments, any device capable of measuring position could be used; LIDAR, RADAR, or properly positioned RGB cameras can provide the necessary information.

In some embodiments, it may be advantageous to use manually placed visible surface markers on the subject to facilitate the process of extracting patient position from camera data. Furthermore, there should be use of anatomical structures to reduce ambiguity of patient position, specifically, topographical features can be recognized on the back such as the" symmetry line" which can complement or in some cases, replace point cloud registrations. For example, by tracking just a line drawn down the patient's back, there would be no need for a predetermined surface model. In all likelihood this would produce nearly identical results to those presented by the present disclosure.

In some cases, it can be assumed that the subject is a rigid subject. In the context of a person standing in a stable posture, attempting not to move, this is a reasonable approximation. However, by using a deformable model of human shape, such as SCAPE or SMPL it can be possible to capture local variations in pose as well. Such a model can potentially improve the results on human subjects.

In a similar vein, the protocol mentioned above only accounts for lateral translations, not rotation. Correcting for rotation may require prior knowledge of the structure of the scan target, for example a spine model. In principle it can be possible to fit a model to the radiographic images, then de-rotate the model and generate a synthetic radiograph.

In some embodiments, an alternative method to perform motion correction that requires no depth cameras at all, may be used. In such embodiments, attaching a radiopaque calibration target to the patient directly may be required. For example, a rigid cylinder perhaps 1 m in length and 1 cm in diameter could be fixed to the dorsal lateral torso, such that it would not interfere with the spine image. Motion correction would consist of fitting a straight line to the radiographic target, then shifting each row of the image to match the fitted line.

Figure 9:
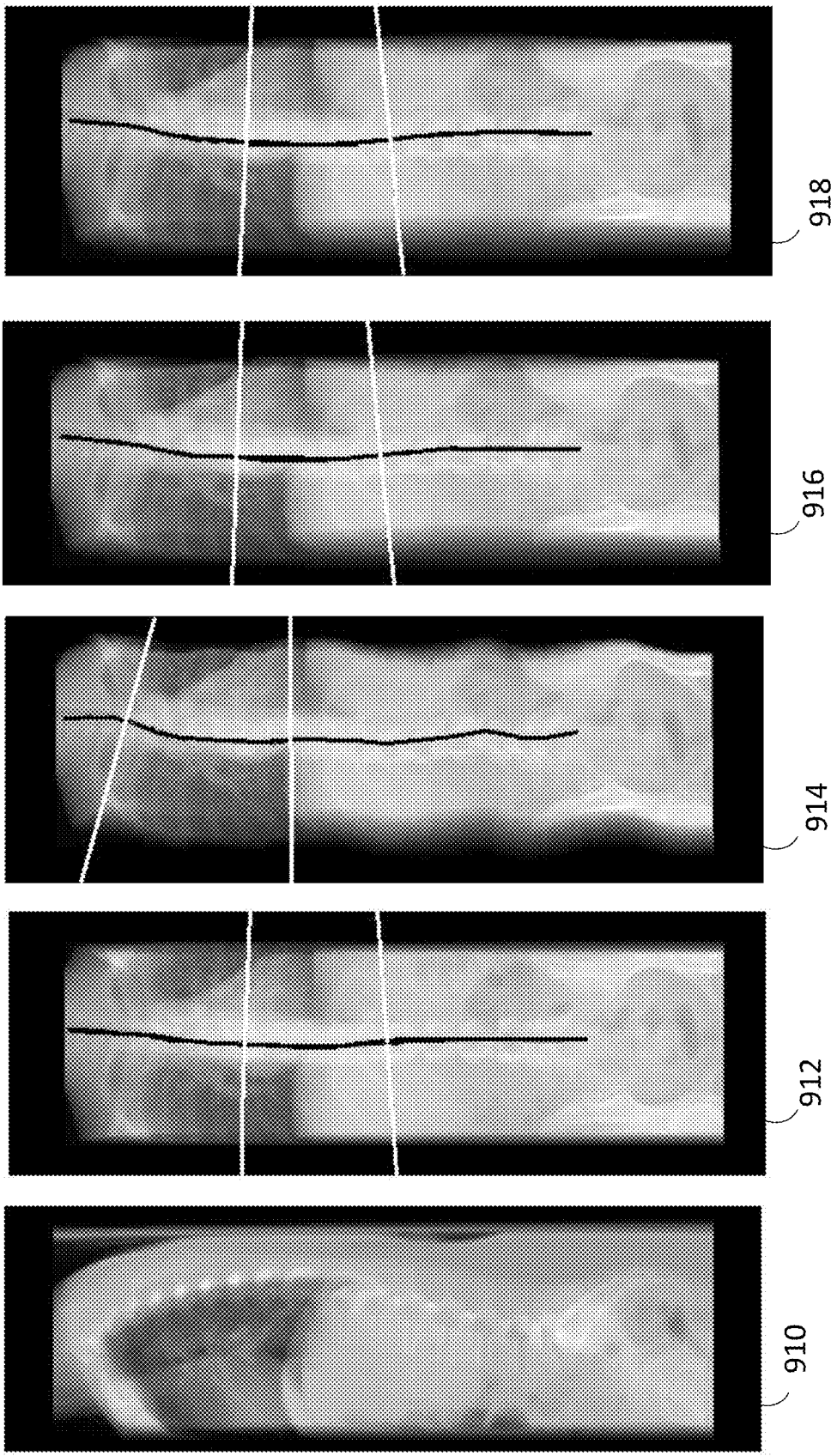
FIG. 9 shows radiographs sampled from a CT volume, utilized in one exemplary embodiments of the present invention.

FIG. 9 shows radiographs sampled from a CT volume, utilized in one exemplary embodiments of the present invention. FIG. 9 shows a static scan in image 910 and frontal (PA) scan in image 912, where projections show the reference spine shape. FIG. 9 also shows a raw image 914 which was simulated with an average movement of 0.3 m/s, wherein a motion correction was applied by Row Shift as shown in image 916 and Warp Field as shown in image 918. The smoothed spline of vertebral subject landmarks is shown in white lines on the frontal (PA) scan in image 912, with the relevant normal for Computer Cobb angles depicted in black.

As a reference to the processes of conducting the basic protocol comprising collaborating, imaging, motion tracking, and corrections of a radiograph, CT scans of 15 healthy adult spines with manually verified segmentations can be downloaded from a publicly available dataset. For each vertebra, a template mesh can be symmetrized and registered to the corresponding CT segment with a seven DoF (dimensions of Freedom) affine transformation.

In one exemplary case, for each spine model (CT subject), random rigid-subject motion can be generated in the frequency domain at 1000 Hz resolution and then be converted to temporal domain. Motion patterns can be generated as axial translation, general translation, pure rotation, or generalized rigid-subject movement.

Synthetic radiographs can be generated by sampling the CT images, pixel values correspond to line integrals along line segments emanating from the X-ray emitter. Volumetric data may be positioned as in the x-ray system scan chamber according to SRS convention. Time steps can be sampled corresponding to each image row: rigid subject motion was sampled from the sequences described above and the transformation applied to the CT volume. Each projected image row was generated by a raytraced algorithm, then rows were stacked to provide the "raw" synthetic radiograph exhibiting motion artifact.

Experimental Results

Physical experiments were carried out to assess the proposed methods in a clinical setting; testing was performed at the Hospital for Special Surgery (HSS) in New York City, NY USA. The scan subject was constructed by embedding a radiographic spine model (Sawbones, Vashon, WA USA) in a rigid torso subject, braced with foam padding. In addition, 16 radiopaque markers were placed on the surface of the subject. The subject was mounted on a platform with spring-loaded support. Spring constants and counterweights were experimentally adjusted to produce motion comparable to excessive sway of a scan patient.

Simultaneous motion tracking: The motion correction techniques described above require external measurement of the motion of the subject during EOS scanning. Marker-based motion capture systems (e.g. Vicon) are a candidate, as they are extremely accurate with more than sufficient temporal resolution. However, such systems are bulky and sensitive to jostling, making them poorly suited to the tight quarters of the EOS scan chamber. Instead, implementation of a marker-less tracking system using off-the-shelf depth cameras was chosen.

Depth imaging: Three stereo depth cameras (e.g., Intel Realsense D435) were mounted to the paneling of the EOS scan chamber, taking care not to obstruct the radiographic field of view. This camera model was selected for its wide viewing angle and lack of coded projections, permitting overlapping scan areas. Depth cameras were connected to an Intel NUC running custom code for synchronous recording.

Depth scans were captured at 30 Hz, the output being a point cloud in local coordinates for each camera. Spatial calibration between the cameras was performed by simultaneously scanning a spherical calibration target in several hundred positions with all cameras. The center of the scanned sphere was located for each camera with a RANSAC sphere-fitting algorithm, and these temporally paired points were used to compute the relative positions of the cameras.

Calibration with EOS: Merged point clouds from the three depth cameras must be brought into SRS coordinates. Calibration with EOS was performed by scanning an object whose position can be accurately measured with both surface scans and radiographic imaging. A customized calibration target was constructed consisting of a Delrin cylinder (40 mm radius, 500 mm length) and a 3D printed ABS sphere (85 mm radius). These components were connected with a metal rod projecting perpendicularly from the axis of the cylinder. This target was scanned both with EOS and the Realsense cameras and the position determined in each coordinate system. Thereafter, the transformation between these coordinate spaces was used to convert all surface scans to SRS global axes.

Figure 10A:
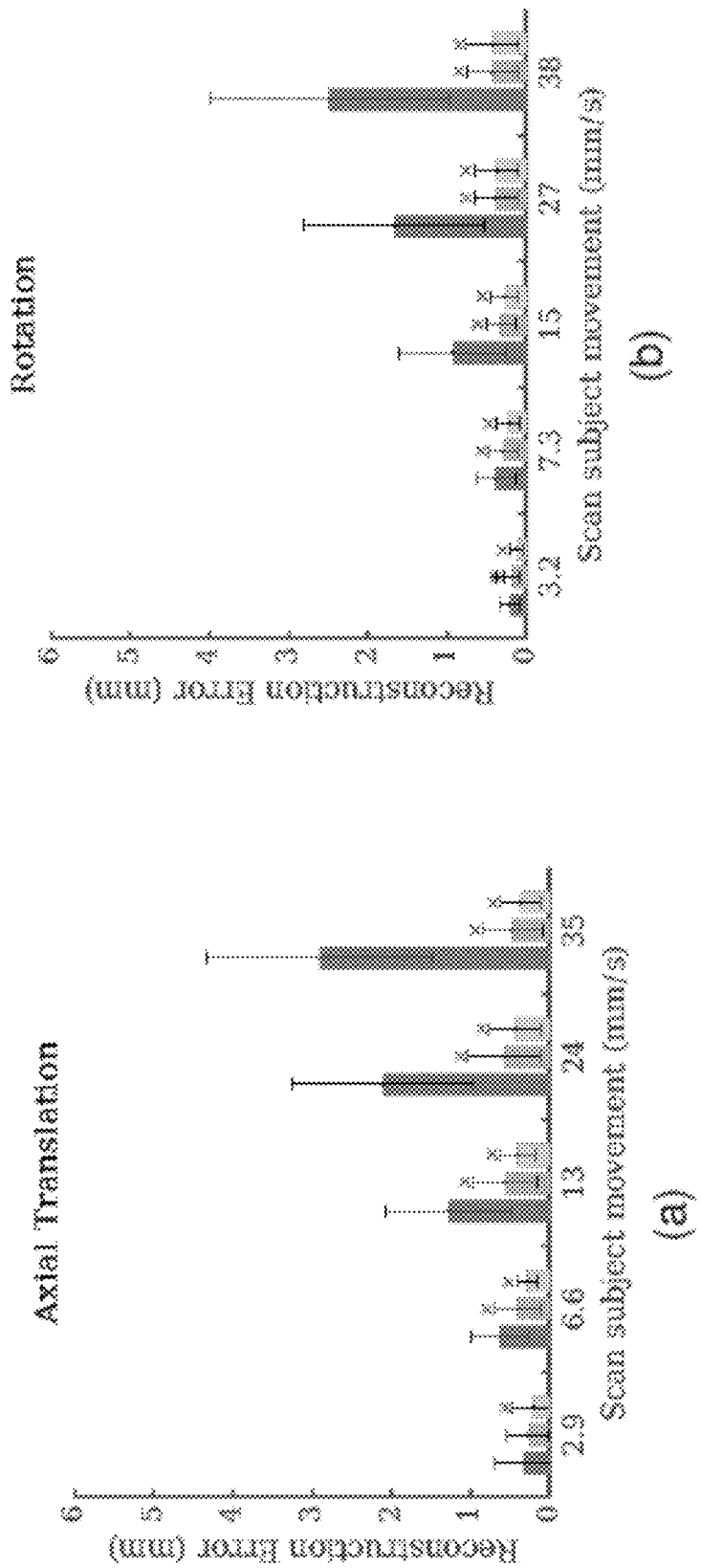
FIGS. 10A-10C show landmark reconstruction error for synthetic trials in Raw Images, Row Shift and Warp Field, according to some embodiments.
Figure 10B:
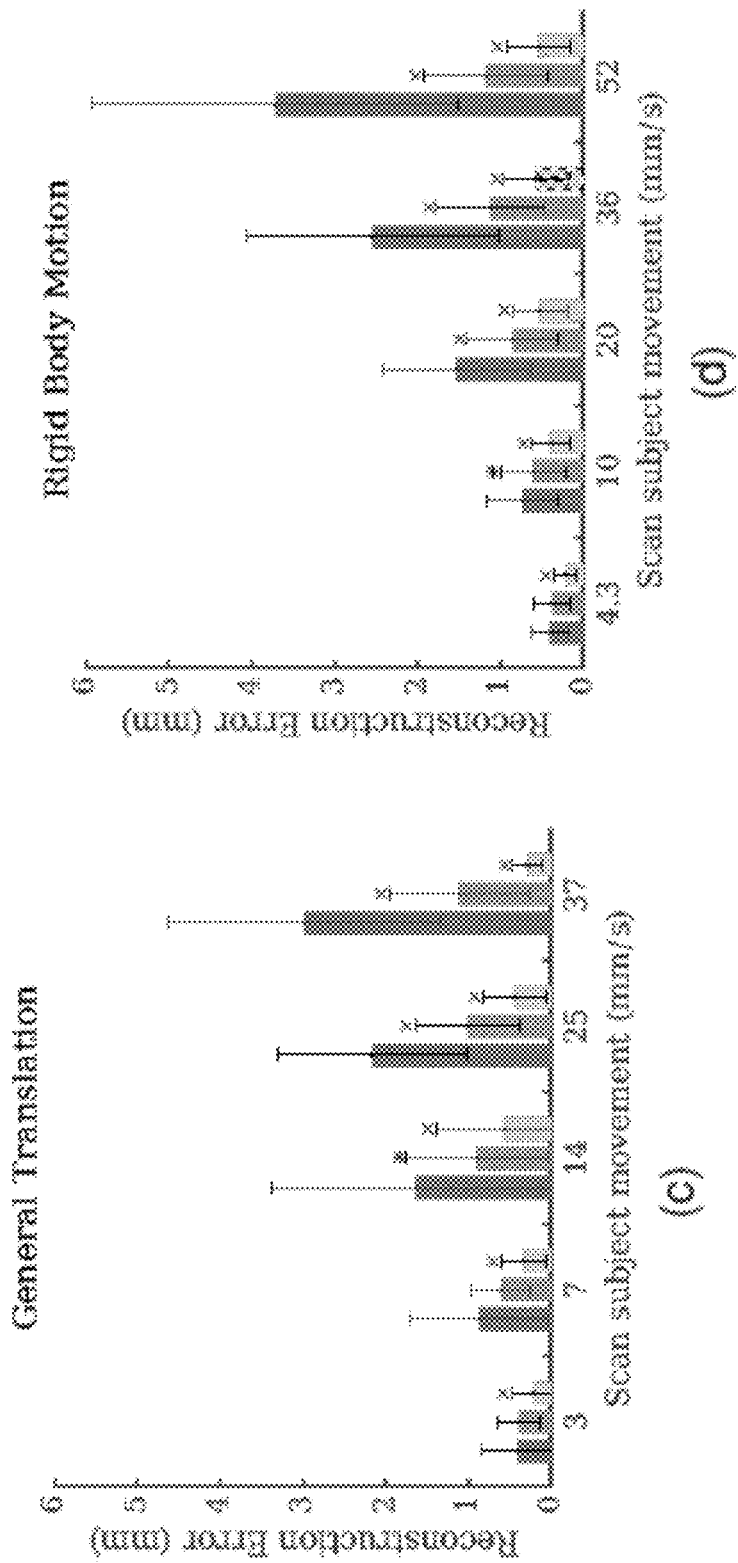
Figure 10C:
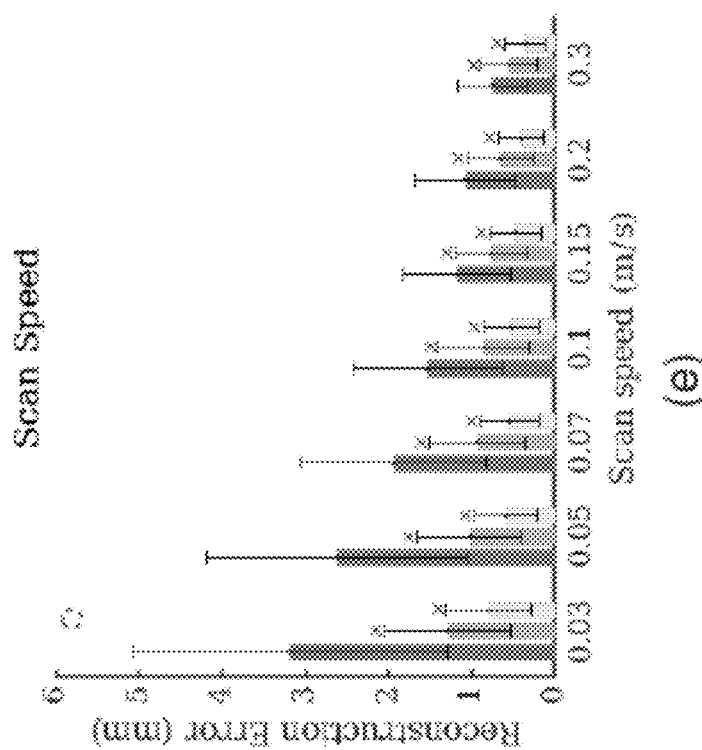

FIGS. 10A-10C show landmark reconstruction error for synthetic trials in Raw Images, Row Shift and Warp Field, according to some embodiments. In FIGS. 10A-10C, the landmark reconstruction error for synthetic trials with error bars indicate +/−1 STD. Statistical difference from raw landmark error is indicated for $p<0.05$ (*) and $p<0.001$ (X).

Temporal Synchronization: It is necessary to find the synchronization between surface scans and radiography. In other words, there is a need the to find the timestamped depth scan corresponding to each row of the EOS image. If it were possible to send or receive a hardware trigger to signal the beginning of the EOS scan (or if the output DICOM header included timestamps with sufficient precision) then this task would be trivial. Lacking this it is necessary to rely on external measurement of the activity of the EOS scanner; a use of the LED indicators mounted to the emitter gantries can be made. The position of the X-ray emitter can be directly measured by attaching photocells to the external paneling of the scanner.

In the current system a microprocessor (e.g., implemented with arduino) continuously reads the analogue voltage of four photocells mounted at 0.5 m vertical intervals and sends the digitized signal to the depth scanning computer. During an EOS scan the gantry-mounted LEDs move past the photocells, eliciting a spike in voltage that provides the temporal correspondence between depth images and radiographic image row. Timestamps for the remaining rows in the image can be extrapolated using the speed of the EOS scan, extracted from the DICOM header.

Several spinal alignment parameters were selected to evaluate the effectiveness of motion correction. All parameters are computed from a set of six standard anatomical landmarks: inferior/superior vertebral bodies and inferior/superior left and right pedicles. All thoracic and lumbar vertebrae were labelled for a total of 108 landmarks per subject spine. For in-silico trials, these landmarks were defined in reference to the registered spine model; planar projections were automatically generated during the synthetic slot scanning. For subject trials, these 2D points were manually identified in frontal and lateral radiographs. In both cases, planar landmark positions were motion corrected using both row shift and warp field techniques, and the 3D position reconstructed by back-projection.

Landmark Reconstruction Error: Raw motion-distorted marker positions are reconstructed in 3D and rigidly registered to the ground truth (static) spine model to minimize squared error; this eliminates error due to global position. This procedure is repeated for motion-corrected landmark positions using both Row Shift and Warp Field strategies.

Computer Cobb Angle: This metric is a two dimensional measure of global reconstruction accuracy. A curve was drawn by splining and smoothing vertebral subject landmarks in the PA image plane. Tangent lines at the level of inter-vertebral disks were intersected to find the maximum angle for each frontal radiograph/

Spine Length: 3D spine length is computed by summing distances between reconstructed vertebral subject landmarks, from lower L5 to upper T1.

Fréchet Distance: This scalar is a measure of similarity between curves, measuring the infimum of the maximum of distances between curves, when traversing each curve monotonically. The discrete Fréchet distance can be computed on a cubic spline interpolation of vertebral subject landmarks.

Figure 11A:
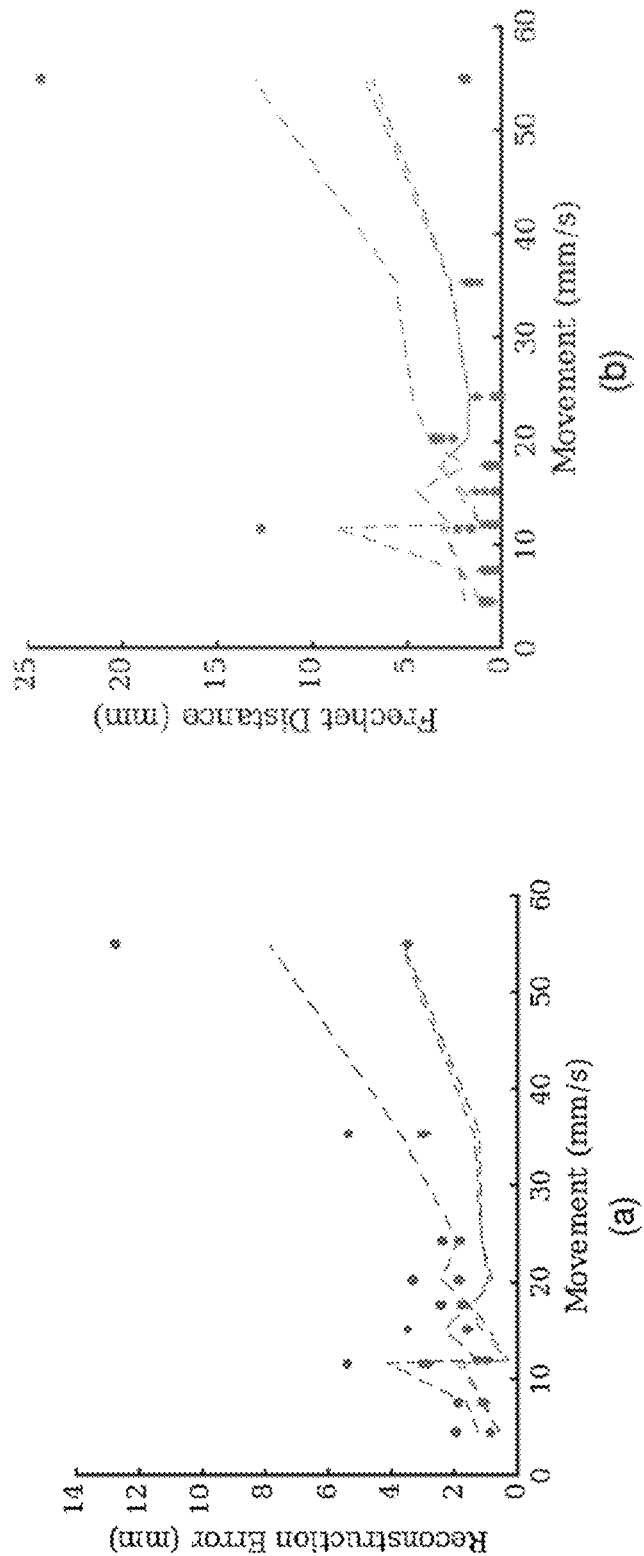
FIGS. 11A-11B show a subject experiments overlaid with synthetic recreations of each physical trial, according to some experiments of an exemplary embodiment of the present invention.
Figure 11B:
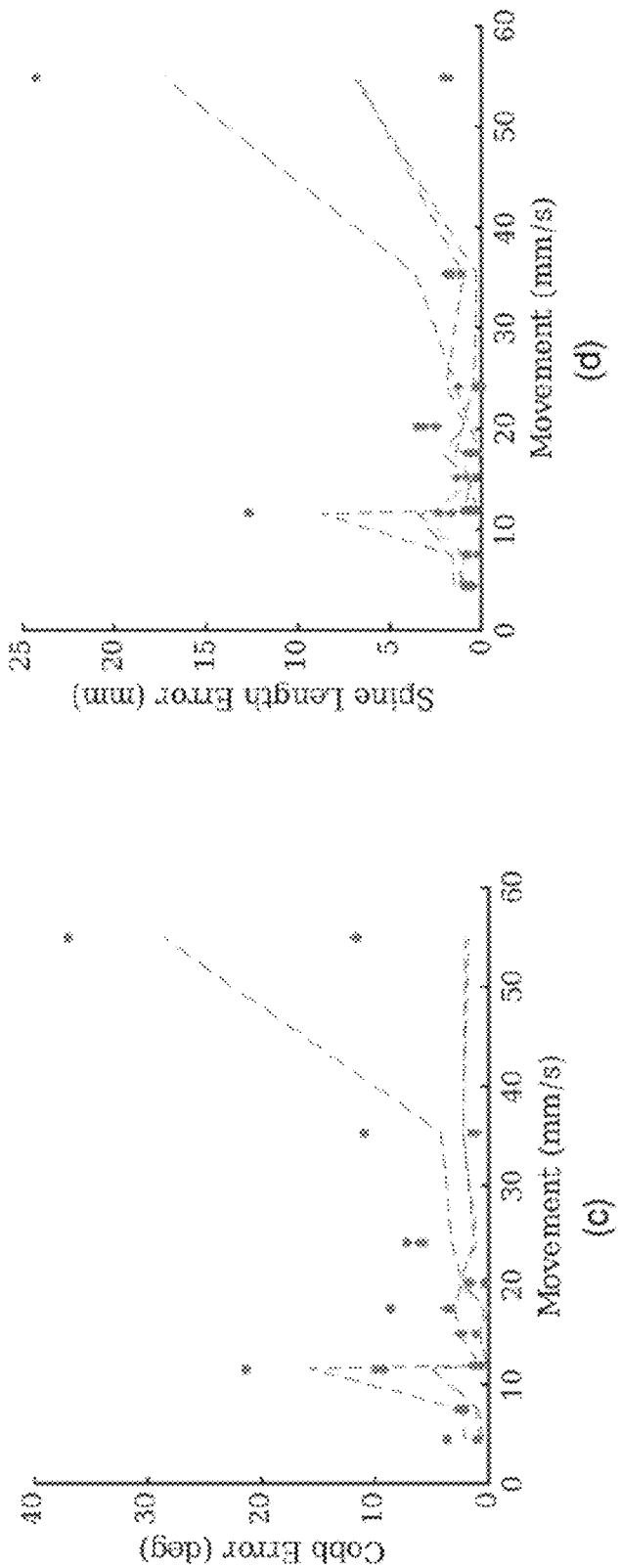

FIGS. 11A-11B show subject experiments overlaid with synthetic recreations of each physical trial, according to some experiments of an exemplary embodiment of the present invention. In FIGS. 11A-11B subject experiments is shown with a raw reconstructions, row shift, and warp field overlaid with synthetic recreations of each physical trial shown in dotted lines.

Simulations

For each CT volume, four classes of motion were generated as described above: axial translation, general translation, rotation, and rigid subject motion. For each class of motion, five levels of magnitude were simulated. In addition, one movement pattern for each spine model was "scanned" at seven different imaging speeds to simulate different scan protocols. A total of 405 pairs (frontal/lateral) of synthetic radiographs were tested using both motion correction strategies described above.

There is no standard metric to quantify patient movement. In order to compare across motion patterns, the average speed of all particles (voxels) located in the bounding box is taken $\{|x|<0.1$ m, $|y|<0.1$ m, $0.8$ m$<z<1.4$ m$\}$ in SRS coordinates. This metric naturally combines rotation and translation (transformation) elements into a single scalar value that summarizes patient movement.

Figure 12:
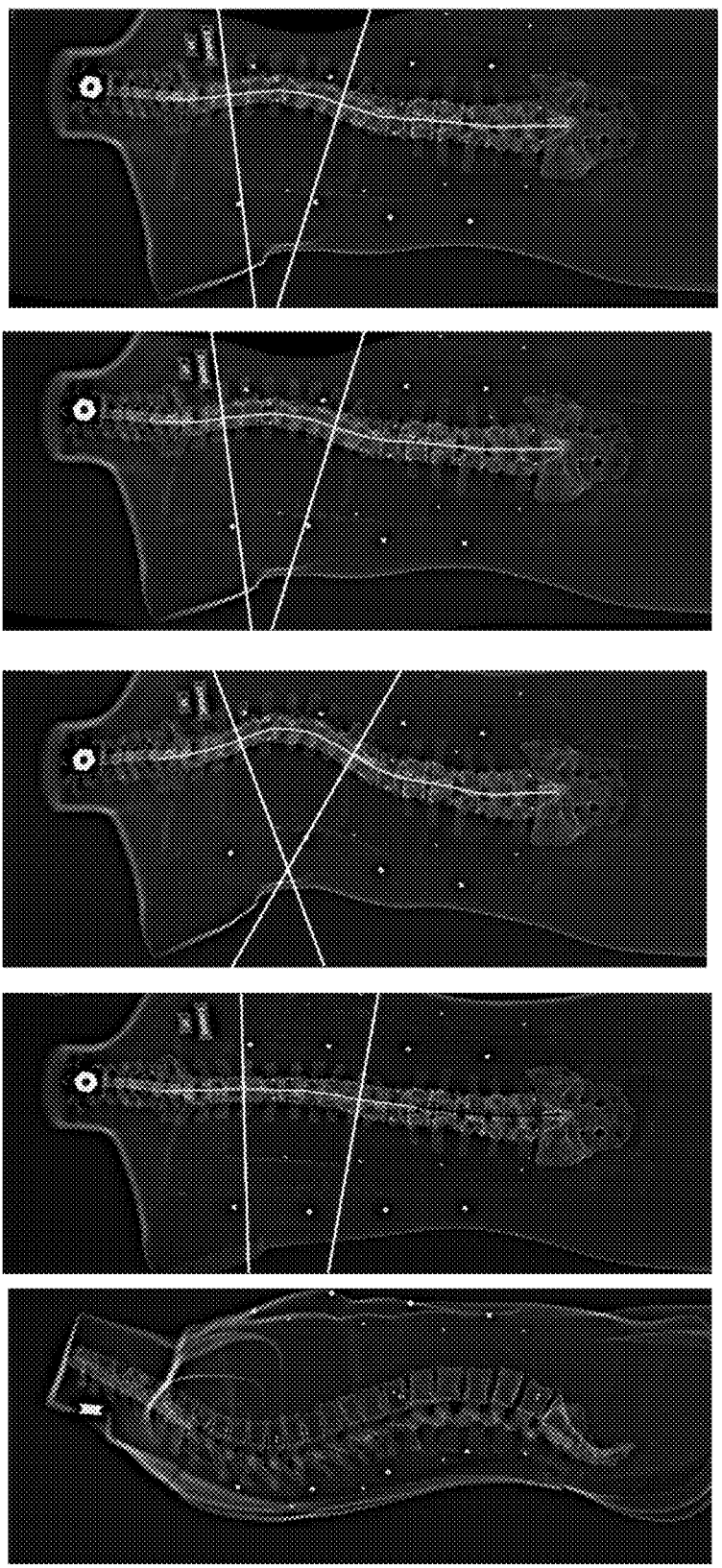
FIG. 12 shows reference radiographic images from subject trials, according to some experiments of an exemplary embodiment of the present invention.

FIG. 12 shows images from subject trials, in one possible embodiment of the present invention. FIG. 12 shows images with (a) and (b) showing the reference spine shape in lateral and frontal radiographs respectively. Motion correction was applied by Row Shift (d) and Warp Field (e). The smoothed spline of vertebral subject landmarks is shown in gray on the frontal images, with the relevant normals for Computer Cobb angles depicted in white.

Phantom Experiments

Three trials were conducted with a scan speed of 0.759 m/s and seven trials at 1.512 m/s. The slower speed is standard of care at HSS, while the faster speed is used for younger patients who have trouble standing still. A static scan of the subject was also collected to use as a ground truth for spinal alignment measurements.

In some embodiments, motion tracking can be performed by fitting a meshed torso model via point-to-surface rigid ICP. For example, the geometry of the torso can be determined a priori using 3dMD6, a validated 3D scanning system with lower than 0:2 mm surface accuracy Reference is made to FIG. 12 showing reference radiographic images from subject trials, according to some experiments of an exemplary embodiment of the present invention. FIG. 12 shows subject experiments with raw reconstructions, row shift, and warp field shown overlaid with synthetic recreations of each physical trial (dotted lines of corresponding pattern).

Table 1 shows experimental results for 10 trials. For each trial, all metrics are computed from the raw image as well as using Row Shift (RS) and Warp Field (WF) motion corrected images.

TABLE 1

| | Experimental Results | | | | | | | | | | | |
|---|---|---|---|---|---|---|---|---|---|---|---|---|
| | Landmark err (mm) | | | Cobb Angle err (°) | | | Spine Length err (mm) | | | Frechet Distance (mm) | | |
| Trial | Raw | RS | WF | Raw | RS | WF | Raw | RS | WF | Raw | RS | WF |
| 1 | 1.987 | 0.880 | 0.885 | 3.671 | 0.989 | 1.052 | 0.927 | 0.784 | 0.577 | 3.131 | 1.198 | 1.194 |
| 2 | 1.877 | 1.124 | 1.082 | 2.173 | 2.593 | 2.548 | 0.756 | 0.296 | 0.948 | 3.676 | 1.917 | 1.962 |
| 3 | 1.315 | 1.049 | 1.006 | 0.636 | 1.382 | 1.326 | 0.670 | 0.958 | 0.370 | 2.429 | 1.536 | 1.579 |
| 4 | 3.324 | 1.887 | 1.862 | 0.296 | 1.708 | 1.782 | 3.491 | 3.112 | 2.542 | 6.117 | 3.423 | 3.504 |
| 5 | 2.436 | 1.820 | 1.698 | 8.689 | 3.310 | 3.729 | 0.551 | 0.213 | 0.829 | 3.917 | 2.944 | 2.893 |
| 6 | 3.504 | 1.616 | 1.609 | 1.117 | 2.290 | 2.554 | 0.325 | 0.855 | 1.372 | 6.647 | 2.649 | 2.605 |
| 7 | 2.387 | 1.809 | 1.848 | 7.203 | 5.787 | 6.088 | 0.374 | 0.002 | 1.323 | 3.825 | 3.281 | 3.375 |
| 8 | 5.376 | 3.074 | 2.967 | 10.92 | 1.522 | 1.135 | 1.651 | 1.161 | 1.881 | 7.554 | 4.689 | 4.510 |
| 9 | 12.77 | 3.519 | 3.480 | 37.03 | 11.56 | 11.74 | 24.30 | 1.825 | 2.039 | 21.46 | 6.036 | 5.523 |
| 10 | 5.422 | 3.038 | 2.846 | 21.42 | 10.01 | 9.263 | 12.65 | 2.340 | 1.664 | 11.96 | 4.804 | 4.394 |
| p | | 0.035 | 0.032 | | 0.083 | 0.086 | | 0.180 | 0.212 | | 0.025 | 0.027 |

Tables 2 and 3 show the efficacy of motion correction at different imaging speeds (labeled S1-S7). Mean error compared to the static scan is shown for 15 trials for each image speed, and Pearson correlation coefficients are presented for each motion correction method (raw indicating no motion correction). As a representative metric of effect size, landmark reconstruction error dropped by 77% using Warp Field correction (55% with Row Shift) across all rigid-subject motion trials.

For the same simulated trials, Cohen's d was computed for each metric to measure effect size of WF (RS) motion correction vs raw reconstructions: 1.50 (1.13) for RMS (root-mean-square) landmark error, 1.15 (1.08) for Fréchet distance, 0.57 (0.57) for Computer Cobb angle, and 0.98 (0.36) for spine length.

Motion tracking was performed by fitting a meshed torso model via point-to-surface rigid ICP. The geometry of the torso was determined a priori using 3dMD, a validated 3D scanning system with below than 0.2 mm surface accuracy. The quality of depth scans (and spatial calibration) can be assessed by the residual scan-to-mesh distance after ICP registration; points <50 mm from the registered mesh were considered as part of the phantom. For all scans across all trials, the median distance (RMS) was 1.8 mm (4.2 mm).

Measures of reconstruction accuracy are presented in Table 1; on average, RMS landmark reconstruction error dropped by 44% using Warp Field correction (42% using Row Shift). For each metric, Cohen's d was computed to measure effect size of WF (RS) motion correction vs raw reconstructions: 0.8 (0.78) for RMS landmark error, 0.83

(0.85) for Fréchet distance, 0.61 (0.62) for Computer Cobb angle, and 0.42 (0.46) for spine length.

Based on only these data it is difficult to determine what portion of the residual reconstruction error is due to parallax effects (as in simulations) and how much is due to inaccuracies in motion tracking, synchronization, manual landmarking, or the assumption of rigid subject motion. Therefore, in addition to the purely synthetic experiments described above, each of the physical experiments is simulated by using the recorded motion to recreate projected landmark positions.

Simulated error is consistently lower than recorded values, indicating that a failure to capture the full magnitude of patient motion—but another possibility is that landmarks are simply harder to identify in distorted images. To resolve this ambiguity the expected position of the 16 radiopaque markers can be computed on the surface of the phantom. These physical markers can be readily identified with negligible labelling error. Reconstruction error for these landmarks was highly correlated with subject motion (R=0.90), implying that additional error in the physical experiments is primarily due to imperfect motion tracking and/or synchronization rather than faulty landmarking.

The methods described here provide a means of performing radiographic image correction without any prior knowledge of the shape of the scanned object. This is important in a clinical setting where the purpose of imaging is diagnostic, so minimal assumptions should be made about the structure being measured.

Motion correction of images is limited by the fact that information is lost in the projection from 3D to planar radiographs as lines are collapsed into points. Perfect image restoration would require knowledge of the distribution of radiopaque material along the x-ray path.

Furthermore, the methods described here are optimized for structures at the isocenter: the row-shift algorithm essentially translates each image row such that the central image column is at the isocenter, while the warp field method deforms each radiograph to match a hypothetical static image at the plane of the isocenter. As a consequence, residual landmark error was correlated with distance from the isocenter in simulated experiments (R=0.45 RS, R=0.51 WF). Reconstructed accuracy of structures distal to the isocenter may even be degraded by these motion correction techniques.

Nevertheless, in silico results clearly demonstrate the overall efficacy of depth-mediated motion correction. With perfect measurement of subject motion and error-free landmark identification, spinal alignment parameters are universally improved. Effect size of motion correction ranged from small (spine length with RS) to very large (landmark RMS distance with WF). Experimental testing with a subject model in a clinical setting confirms this result, with some additional noise due to imperfect motion tracking.

Despite these limitations, the system demonstrably improves image quality and spinal alignment measurements. Subjectively, motion artifact is greatly reduced in motion corrected images, as can be seen by the elimination of discontinuities on the edges of the torso. Furthermore, while improvements in some alignment parameters did not rise to the level of statistical significance (e.g. Cobb Angle) closer inspection reveals that many trials simply did not exhibit much deviation from ground truth. For those trials that did show substantial distortion (e.g. Cobb Angle error >6^o), both motion correction schemes greatly reduced the error (57% WF/58% RS, N=5).

This disclosure describes a new method for intermodal motion correction in slot scanners. The techniques described here are presented in the context of standing EOS biplanar radiography, but can be readily extended e.g. to DXA or digital mammography. The key innovation is augmenting existing radiography systems with high speed surface imaging, including the necessary calibration and synchronization protocols. In the experimental setup, a significant portion of residual error after motion correction appears to come from technical deficiencies.

In fact, perhaps the most clinically relevant result of this research is to establish expected error distributions for clinical parameters as a function of patient motion. What is missing is a reliable assessment of typical patient movement during standing EOS scans. These scans, together with results presented here, may enable a user to determine how much error in spinal alignment parameters is currently being generated due to patient motion.

It should be noted that there does exist a simple alternative for motion correction that can be implemented in any EOS scanner with minimal effort: simply attach a radiopaque rod to the patient. A vertical rod should appear on both PA and lateral images as a straight line, and row-shift motion correction can be performed as described in Section 2.2.2 to correct any "waves" in this line. Without a more complicated calibration target it would be impossible to detect vertical motion or rotation, but as seen in synthetic results even a simple row-shift motion correction scheme can significantly ameliorate motion artifact.

TABLE 2

Landmark Error and Fréchet distance

| | Reconstructed Landmark Error | | | | | | Fréchet Distance | | | | | |
|---|---|---|---|---|---|---|---|---|---|---|---|---|
| | Raw | | Row Shift | | Warp Field | | Raw | | Row Shift | | Warp Field | |
| | rms | | std | | rms | | std | | rms | | std | |
| A1 | 0.270 | 0.057 | 0.022 | 0.004 | 0.018 | 0.002 | 0.554 | 0.162 | 0.050 | 0.015 | 0.040 | 0.009 |
| A2 | 0.664 | 0.165 | 0.049 | 0.009 | 0.040 | 0.005 | 1.316 | 0.420 | 0.120 | 0.028 | 0.084 | 0.019 |
| A3 | 1.345 | 0.490 | 0.095 | 0.022 | 0.079 | 0.010 | 2.566 | 0.975 | 0.234 | 0.074 | 0.176 | 0.032 |
| A4 | 2.349 | 0.670 | 0.160 | 0.036 | 0.134 | 0.017 | 4.530 | 1.505 | 0.385 | 0.093 | 0.312 | 0.085 |
| A5 | 3.213 | 0.659 | 0.201 | 0.062 | 0.188 | 0.027 | 5.944 | 1.511 | 0.486 | 0.185 | 0.440 | 0.132 |
| T1 | 0.350 | 0.060 | 0.239 | 0.037 | 0.020 | 0.002 | 0.620 | 0.111 | 0.448 | 0.090 | 0.043 | 0.006 |
| T2 | 0.766 | 0.153 | 0.352 | 0.123 | 0.043 | 0.005 | 1.517 | 0.436 | 0.648 | 0.224 | 0.089 | 0.017 |
| T3 | 1.371 | 0.322 | 0.481 | 0.194 | 0.086 | 0.009 | 2.520 | 0.873 | 0.905 | 0.412 | 0.174 | 0.025 |
| T4 | 2.247 | 0.437 | 0.870 | 0.411 | 0.144 | 0.022 | 4.107 | 1.192 | 1.454 | 0.755 | 0.325 | 0.077 |
| T5 | 3.448 | 0.724 | 1.275 | 0.513 | 0.194 | 0.025 | 6.420 | 2.313 | 2.300 | 1.454 | 0.393 | 0.104 |
| R1 | 0.244 | 0.061 | 0.113 | 0.028 | 0.112 | 0.028 | 0.449 | 0.117 | 0.248 | 0.063 | 0.248 | 0.063 |

TABLE 2-continued

Landmark Error and Fréchet distance

| | Reconstructed Landmark Error | | | | | | Fréchet Distance | | | | | |
|---|---|---|---|---|---|---|---|---|---|---|---|---|
| | Raw | | Row Shift | | Warp Field | | Raw | | Row Shift | | Warp Field | |
| | rms | std | rms | std | rms | std | rms | std | rms | std | rms | std |
| R2 | 0.459 | 0.112 | 0.188 | 0.073 | 0.185 | 0.072 | 0.801 | 0.207 | 0.424 | 0.163 | 0.419 | 0.162 |
| R3 | 1.134 | 0.364 | 0.265 | 0.085 | 0.266 | 0.086 | 2.316 | 0.824 | 0.628 | 0.177 | 0.623 | 0.184 |
| R4 | 2.021 | 0.505 | 0.430 | 0.198 | 0.429 | 0.198 | 4.170 | 1.116 | 0.994 | 0.437 | 1.012 | 0.460 |
| R5 | 2.965 | 0.493 | 0.522 | 0.187 | 0.517 | 0.193 | 5.610 | 1.428 | 1.149 | 0.439 | 1.150 | 0.406 |
| G1 | 0.462 | 0.081 | 0.279 | 0.049 | 0.108 | 0.024 | 0.890 | 0.172 | 0.474 | 0.082 | 0.219 | 0.054 |
| G2 | 0.862 | 0.170 | 0.391 | 0.117 | 0.201 | 0.065 | 1.764 | 0.486 | 0.691 | 0.253 | 0.397 | 0.156 |
| G3 | 1.788 | 0.404 | 0.746 | 0.221 | 0.464 | 0.188 | 3.404 | 0.901 | 1.324 | 0.447 | 0.963 | 0.416 |
| G4 | 2.966 | 0.754 | 1.164 | 0.337 | 0.665 | 0.219 | 5.928 | 1.790 | 1.848 | 0.481 | 1.486 | 0.434 |
| G5 | 4.356 | 0.997 | 1.390 | 0.347 | 0.672 | 0.282 | 8.050 | 1.693 | 2.612 | 0.908 | 1.483 | 0.644 |
| S1 | 3.786 | 0.538 | 1.476 | 0.378 | 1.049 | 0.338 | 7.400 | 1.246 | 2.954 | 0.896 | 2.481 | 0.883 |
| S2 | 3.081 | 0.645 | 1.050 | 0.233 | 0.758 | 0.166 | 5.770 | 1.351 | 2.193 | 0.671 | 1.987 | 0.600 |
| S3 | 2.253 | 0.537 | 0.730 | 0.291 | 0.422 | 0.138 | 4.075 | 1.053 | 1.194 | 0.503 | 0.892 | 0.344 |
| S4 | 1.788 | 0.404 | 0.746 | 0.221 | 0.464 | 0.188 | 3.404 | 0.901 | 1.324 | 0.447 | 0.963 | 0.416 |
| S5 | 1.350 | 0.316 | 0.471 | 0.117 | 0.285 | 0.078 | 2.489 | 0.712 | 0.784 | 0.241 | 0.565 | 0.159 |
| S6 | 1.243 | 0.262 | 0.436 | 0.142 | 0.242 | 0.071 | 2.139 | 0.472 | 0.722 | 0.236 | 0.547 | 0.171 |
| S7 | 0.863 | 0.163 | 0.315 | 0.116 | 0.187 | 0.060 | 1.563 | 0.444 | 0.573 | 0.242 | 0.342 | 0.130 |

Table 2 shows Landmark Error and Fréchet distance for synthetic trials. Rows A1-A5 show results for increasing magnitudes of pure axial translation, T1-T5 for translation, R1-R5 for pure rotation, and G1-G5 for general rigid-subject transformations. S1-S7 show the effect of different scan speeds on a single motion pattern. Distances are computed in mm. Both motion correction techniques significantly reduced error ($p<0.001$) in all experiments.

This simplified protocol also provides a clue to the greater potential of surface-mediated motion correction. Because the entire patient can be scanned every 33 ms, there is no need to assume rigid-subject motion in real patients. If instead a human surface subject model was implemented, anew pose could be fitted to every depth scan. In previous work a non-rigid surface modeling was integrated to a radiographic environment. Future research may be focused on extending the methods described here to account for shifts in patient posture such as minor twisting and bending

TABLE 3

Computer Cobb angle and spine length

| | Computer Cobb Angle | | | | | | Spine Length | | | | | |
|---|---|---|---|---|---|---|---|---|---|---|---|---|
| | Raw | | Row | | Warp Field | | Raw | | Row Shift | | Warp Field | |
| | Mean Err (°) | R | Mean Err (°) | R | Mean Err (°) | R | Mean Err (°) | R | Mean Err (°) | R | Mean Err (°) | R |
| A1 | 0.367 | 0.994 | 0.174 | 0.999 | 0.185 | 0.999 | 0.151 | 1.000 | 0.012 | 1.000 | 0.013 | 1.000 |
| A2 | 0.882 | 0.977 | 0.328 | 0.997 | 0.327 | 0.997 | 0.319 | 1.000 | 0.032 | 1.000 | 0.033 | 1.000 |
| A3 | 1.415 | 0.908 | 0.395 | 0.995 | 0.431 | 0.994 | 0.543 | 1.000 | 0.051 | 1.000 | 0.048 | 1.000 |
| A4 | 2.403 | 0.784 | 0.343 | 0.997 | 0.446 | 0.995 | 1.009 | 0.999 | 0.124 | 1.000 | 0.083 | 1.000 |
| A5 | 5.229 | 0.570 | 0.238 | 0.998 | 0.419 | 0.992 | 3.030 | 0.999 | 0.103 | 1.000 | 0.168 | 1.000 |
| T1 | 0.474 | 0.991 | 0.165 | 0.999 | 0.171 | 0.999 | 0.784 | 1.000 | 0.764 | 1.000 | 0.015 | 1.000 |
| T2 | 0.772 | 0.973 | 0.302 | 0.997 | 0.310 | 0.997 | 1.141 | 1.000 | 1.037 | 1.000 | 0.029 | 1.000 |
| T3 | 1.167 | 0.948 | 0.335 | 0.997 | 0.396 | 0.994 | 1.090 | 0.999 | 0.997 | 0.999 | 0.070 | 1.000 |
| T4 | 4.131 | 0.089 | 0.305 | 0.996 | 0.340 | 0.994 | 1.464 | 0.997 | 1.570 | 0.997 | 0.136 | 1.000 |
| T5 | 6.174 | 0.685 | 0.344 | 0.995 | 0.420 | 0.995 | 4.788 | 0.989 | 2.880 | 0.992 | 0.148 | 1.000 |
| R1 | 1.255 | 0.937 | 0.937 | 0.974 | 0.939 | 0.974 | 0.108 | 1.000 | 0.058 | 1.000 | 0.029 | 1.000 |
| R2 | 1.336 | 0.946 | 1.658 | 0.915 | 1.658 | 0.914 | 0.185 | 1.000 | 0.094 | 1.000 | 0.050 | 1.000 |
| R3 | 2.534 | 0.838 | 2.033 | 0.879 | 1.729 | 0.897 | 0.686 | 1.000 | 0.090 | 1.000 | 0.104 | 1.000 |
| R4 | 2.239 | 0.762 | 0.927 | 0.973 | 0.969 | 0.970 | 1.049 | 0.999 | 0.170 | 1.000 | 0.099 | 1.000 |
| R5 | 2.469 | 0.793 | 1.231 | 0.882 | 1.235 | 0.875 | 1.214 | 0.998 | 0.399 | 1.000 | 0.265 | 1.000 |
| G1 | 1.088 | 0.946 | 0.791 | 0.981 | 0.791 | 0.980 | 0.893 | 1.000 | 0.779 | 1.000 | 0.046 | 1.000 |
| G2 | 1.148 | 0.959 | 1.414 | 0.934 | 1.446 | 0.929 | 1.196 | 0.999 | 0.915 | 1.000 | 0.110 | 1.000 |
| G3 | 2.311 | 0.877 | 1.768 | 0.911 | 1.615 | 0.919 | 1.657 | 0.998 | 1.346 | 0.998 | 0.166 | 1.000 |
| G4 | 3.293 | 0.392 | 0.934 | 0.971 | 0.967 | 0.969 | 2.771 | 0.995 | 2.072 | 0.997 | 0.328 | 1.000 |
| G5 | 5.109 | 0.611 | 1.503 | 0.953 | 1.446 | 0.954 | 4.126 | 0.991 | 2.659 | 0.996 | 0.486 | 1.000 |
| S1 | 5.881 | 0.585 | 2.827 | 0.861 | 2.957 | 0.940 | 3.686 | 0.995 | 2.493 | 0.999 | 0.282 | 1.000 |
| S2 | 4.038 | 0.647 | 2.459 | 0.802 | 2.414 | 0.798 | 1.806 | 0.997 | 1.448 | 0.998 | 0.396 | 1.000 |
| S3 | 2.204 | 0.734 | 1.348 | 0.942 | 1.334 | 0.942 | 2.056 | 0.995 | 1.130 | 0.999 | 0.301 | 1.000 |
| S4 | 2.311 | 0.877 | 1.768 | 0.911 | 1.615 | 0.919 | 1.657 | 0.998 | 1.346 | 0.998 | 0.166 | 1.000 |
| S5 | 2.819 | 0.712 | 1.863 | 0.908 | 1.727 | 0.919 | 0.912 | 0.999 | 0.614 | 1.000 | 0.152 | 1.000 |
| S6 | 1.521 | 0.916 | 1.428 | 0.916 | 1.447 | 0.911 | 0.977 | 0.999 | 0.607 | 1.000 | 0.120 | 1.000 |
| S7 | 0.950 | 0.964 | 1.169 | 0.957 | 1.063 | 0.967 | 0.703 | 1.000 | 0.492 | 1.000 | 0.080 | 1.0 |

Table 3 shows Computer Cobb angle and spine length are computed in degrees and millimeters respectively. Rows A1-A5 show results for increasing magnitudes of pure axial translation, T1-T5 for translation, R1-R5 for pure rotation, and G1-G5 for general rigid-subject transformations. S1-S7 show the effect of different scan speeds on a single motion pattern. Pearson's correlation coefficient (R) is computed compared to ground truth values.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or system, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage system, a magnetic storage system, or any suitable combination of the foregoing. In the context of this document, a computer readable storage medium may be any tangible medium that can contain or store a program for use by or in connection with an instruction execution system, apparatus, or system.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or system.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It may be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other systems to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other systems to cause a series of operational steps to be performed on the computer, other programmable apparatus or other systems to produce a computer implemented method such that the instructions which execute on the computer or other programmable apparatus provide methods for implementing the functions/acts specified in the flowchart and/or block diagram block or blocks.

The flowcharts and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It may also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration but are not intended to be exhaustive or limited to the embodiments disclosed. Many modifications and variations may be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The invention claimed is:

1. A method comprising:
receiving a radiographic image dataset representing a radiographic scan of a region of a human subject;
receiving three-dimensional (3D) image data, acquired during said radiographic scan, representing an optical scan of a surface of said region, wherein said 3D image data is acquired simultaneously with said radiographic scan of said human subject;
fitting a surface model of the subject based to the 3D image data
synchronizing said optical scan with said radiographic scan in a time-dependent manner based, at least in part, on a known pixel sampling pitch of said radiographic scan;
tracking a time-dependent motion of said subject during said acquisition within a region, relative to a specified position, based, at least in part, on said 3D image data, by registering said surface model to said optical scan; and
using said tracking to determine corrections for said radiographic image dataset, based, at least in part, on a known transformation between corresponding coordinate systems of said radiographic image dataset and said surface model.

2. The method of claim 1, wherein said radiographic image dataset is acquired using a slot-scanning method.

3. The method of claim 2, wherein said radiographic image dataset is acquired using a biplanar scanning method.

4. The method of claim 1, wherein said 3D image data comprises at least one of a point cloud, triangulated meshes, and splined surfaces.

5. The method of claim 1, wherein said motion comprises at least one of vertical motion, lateral motion, translational motion, and rotational motion.

6. A system comprising:
at least one hardware processor; and
a non-transitory computer-readable storage medium having stored thereon program code, the program code executable by the at least one hardware processor to:
receive a radiographic image dataset representing a radiographic scan of a region of a human subject,
receive three-dimensional (3D) image data, acquired during said radiographic 3D scan, representing an optical scan of a surface of said region, wherein said 3D image data is acquired simultaneously with said radiographic scan of said human subject;
fit a surface model of the subject based to the 3D image data;
synchronize said optical scan with said radiographic scan in a time-dependent manner based, at least in part, on a known pixel sampling pitch of said radiographic scan,
track a time-dependent motion of said subject during said acquisition within the region of said human subject, relative to a specified position, based, at least in part, on said 3D image data registered to said surface model of the human subject, and
use said track to determine corrections for said radiographic image dataset, based, at least in part, on a known transformation between corresponding coordinate systems of said radiographic image dataset and said 3D image data.

7. The system of claim 6, wherein said radiographic image dataset is acquired using a slot-scanning method.

8. The system of claim 7, wherein said radiographic image dataset is acquired using a biplanar scanning method.

9. The system of claim 6, wherein said 3D image data comprises at least one of a point cloud, triangulated meshes, and splined surfaces.

10. The system of claim 6, wherein said motion comprises at least one of vertical motion, lateral motion, translational motion, and rotational motion.

11. A computer program product comprising a non-transitory computer-readable storage medium having program code embodied therewith, the program code executable by at least one hardware processor to:
receive three-dimensional (3D) image data, acquired during said radiographic 3D scan, representing an optical scan of a surface of said region, wherein said 3D image data is acquired simultaneously with said radiographic scan of said human subject;
fit a surface model of the subject based to the 3D image data;
synchronize said optical scan with said radiographic scan in a time-dependent manner based, at least in part, on a known pixel sampling pitch of said radiographic scan,
track a time-dependent motion of said subject during said acquisition within the region of said human subject, relative to a specified position, based, at least in part, on said 3D image data registered to said surface model of the human subject, and
use said tracking to determine corrections for said radiographic image dataset, based, at least in part, on a known transformation between corresponding coordinate systems of said radiographic image dataset and said 3D image data.

12. The computer program product of claim 11, wherein said radiographic image dataset is acquired using a slot-scanning method.

13. The computer program product of claim 11, wherein said radiographic image dataset is acquired using a biplanar scanning method.

14. The computer program product of claim 11, wherein said 3D image data comprises at least one of a point cloud, triangulated meshes, and splined surfaces.

15. The computer program product of claim 11, wherein said motion comprises at least one of vertical motion, lateral motion, translational motion, and rotational motion.

* * * * *